US009855181B2

(12) United States Patent
Caires et al.

(10) Patent No.: US 9,855,181 B2
(45) Date of Patent: Jan. 2, 2018

(54) TRANSMISSION ASSEMBLY FOR USE IN AN EXOSKELETON APPARATUS

(71) Applicant: BIONIK LABORATORIES, INC., Toronto (CA)

(72) Inventors: Thiago Caires, Toronto (CA); Michal Prywata, Toronto (CA)

(73) Assignee: BIONIK LABORATORIES, INC., Toronto, Ontario (CA)

( * ) Notice: Subject to any disclaimer, the term of this patent is extended or adjusted under 35 U.S.C. 154(b) by 856 days.

(21) Appl. No.: 13/838,738

(22) Filed: Mar. 15, 2013

(65) Prior Publication Data

US 2014/0276261 A1 Sep. 18, 2014

(51) Int. Cl.
*A61H 1/02* (2006.01)
*A61F 5/01* (2006.01)
*A61H 3/00* (2006.01)

(52) U.S. Cl.
CPC ............... *A61H 1/024* (2013.01); *A61F 5/01* (2013.01); *A61F 5/0123* (2013.01); *A61H 1/0244* (2013.01); *A61H 1/0277* (2013.01); *A61H 1/0281* (2013.01); *A61H 3/00* (2013.01); *A61F 2005/0134* (2013.01); *A61H 2201/0103* (2013.01); *A61H 2201/1463* (2013.01); *A61H 2201/165* (2013.01); *A61H 2201/5007* (2013.01); *A61H 2201/5071* (2013.01)

(58) Field of Classification Search
CPC ...... A61H 1/02; A61H 1/0237–1/0244; A61H 1/0277; A61H 2001/0203–2001/0211; A61H 3/00; A61H 2003/007; A61H 2201/12–2201/1215; A61H 2201/1463; A61H 2201/1671; A61H 2201/1676; A61H 2205/102; A61H 2205/106–2205/108; A61F 2002/5038–2002/5043; A61F 5/0104–5/0106; A61F 5/0123–5/0125; A61F 2005/0137–2005/0139
See application file for complete search history.

(56) References Cited

U.S. PATENT DOCUMENTS

| 2,567,195 A | 9/1951 | Ellery |
| 3,551,914 A | 1/1971 | Woodall |
| 3,581,740 A | 6/1971 | Sherbourne |

(Continued)

FOREIGN PATENT DOCUMENTS

| CA | 2724085 | 11/2009 |
| CA | 2728340 | 1/2010 |

(Continued)

OTHER PUBLICATIONS

International Search Report and Written Opinion received in connection to corresponding International Application No. PCT/CA2014/000193, dated Jun. 13, 2014.

(Continued)

*Primary Examiner* — Rachel Young
(74) *Attorney, Agent, or Firm* — Paul R. Horbal; Bereskin & Parr LLP/S.E.N.C.R.L., s.r.l.

(57) ABSTRACT

An exoskeleton for a limb of a user wherein the limb has an upper portion that is pivotally mounted to another part of the exoskeleton about a pivot axis and the upper portion is drivingly connected to the exoskeleton by a force applied via a drive force transmission axis that is vertically offset from the pivot axis.

20 Claims, 30 Drawing Sheets

(56) References Cited

U.S. PATENT DOCUMENTS

| | | | |
|---|---|---|---|
| 3,868,952 A | 3/1975 | Hatton | |
| 3,883,053 A | 5/1975 | Pritchard | |
| 3,993,056 A | 11/1976 | Rabischong | |
| 4,306,320 A | 12/1981 | Delp | |
| 4,364,128 A | 12/1982 | Mummert | |
| 4,573,455 A | 3/1986 | Hoy | |
| 4,628,945 A | 12/1986 | Johnson | |
| 4,697,808 A | 10/1987 | Larson | |
| 4,993,409 A | 2/1991 | Grim | |
| 5,020,515 A | 6/1991 | Mann | |
| 5,030,239 A | 7/1991 | Copes | |
| 5,042,799 A | 8/1991 | Stanley | |
| 5,139,525 A | 8/1992 | Kristinsson | |
| 5,144,943 A | 9/1992 | Luttrell | |
| 5,224,403 A * | 7/1993 | Rueb | B25B 23/1427 |
| | | | 81/477 |
| 5,282,460 A | 2/1994 | Boldt | |
| 5,385,538 A | 1/1995 | Mann | |
| 5,425,780 A | 6/1995 | Flatt | |
| 5,462,517 A | 10/1995 | Mann | |
| 5,487,197 A | 1/1996 | Iskra | |
| 5,514,081 A | 5/1996 | Mann | |
| 5,626,557 A | 5/1997 | Mann | |
| 5,662,693 A | 9/1997 | Johnson | |
| 5,888,213 A | 3/1999 | Sears | |
| 5,961,541 A | 10/1999 | Ferrati | |
| 6,045,524 A | 4/2000 | Hayashi | |
| 6,168,056 B1 | 1/2001 | Bertholon | |
| 6,171,272 B1 | 1/2001 | Akita | |
| 6,361,570 B1 | 3/2002 | Gow | |
| 6,379,393 B1 | 4/2002 | Mavroidis | |
| 6,669,660 B2 | 12/2003 | Branch | |
| 6,863,695 B2 | 3/2005 | Doddroe | |
| 7,190,141 B1 | 3/2007 | Ashrafiuon | |
| 7,204,814 B2 | 4/2007 | Peles | |
| 7,390,309 B2 | 6/2008 | Dariush | |
| 7,429,253 B2 | 9/2008 | Shimada | |
| 7,448,522 B2 | 11/2008 | Collier | |
| 7,479,121 B2 | 1/2009 | Branch | |
| 7,544,172 B2 * | 6/2009 | Santos-Munne | A61H 3/008 |
| | | | 601/5 |
| 7,549,969 B2 | 6/2009 | van den Bogert | |
| 7,731,670 B2 | 6/2010 | Aguirre-Ollinger | |
| 7,731,674 B2 | 6/2010 | Ashihara | |
| 7,819,926 B1 | 10/2010 | Longino | |
| 7,998,096 B1 * | 8/2011 | Skoog | A61H 3/00 |
| | | | 601/35 |
| 8,096,965 B2 | 1/2012 | Goffer | |
| 8,231,688 B2 | 7/2012 | Fairbanks | |
| 8,870,801 B2 | 10/2014 | Tomiyama | |
| 2001/0018565 A1 | 8/2001 | Branch | |
| 2003/0093021 A1 | 5/2003 | Goffer | |
| 2003/0114892 A1 | 6/2003 | Nathan | |
| 2003/0115954 A1 | 6/2003 | Zemlyakov | |
| 2004/0102723 A1 | 5/2004 | Horst | |
| 2005/0102111 A1 | 5/2005 | Dariush | |
| 2006/0052732 A1 | 3/2006 | Shimada et al. | |
| 2006/0064047 A1 | 3/2006 | Shimada et al. | |
| 2006/0117464 A1 | 6/2006 | Capstran | |
| 2006/0149338 A1 | 7/2006 | Flaherty | |
| 2006/0179577 A1 | 8/2006 | Chaffee | |
| 2006/0247904 A1 | 11/2006 | Dariush | |
| 2007/0106190 A1 | 5/2007 | Katoh et al. | |
| 2008/0009771 A1 | 1/2008 | Perry | |
| 2008/0077057 A1 | 3/2008 | Peles | |
| 2008/0097269 A1 | 4/2008 | Weinberg | |
| 2008/0132818 A1 | 6/2008 | Livorsi | |
| 2008/0249438 A1 | 10/2008 | Agrawal | |
| 2009/0255531 A1 | 10/2009 | Johnson | |
| 2009/0292369 A1 | 11/2009 | Kazerooni | |
| 2009/0306564 A1 | 12/2009 | Hirata | |
| 2010/0023133 A1 | 1/2010 | Fairbanks | |
| 2010/0094182 A1 | 4/2010 | Noda | |
| 2010/0094185 A1 | 4/2010 | Amundson | |
| 2010/0094188 A1 | 4/2010 | Goffer | |
| 2010/0198124 A1 | 8/2010 | Bhugra | |
| 2011/0009787 A1 | 1/2011 | Pallari | |
| 2011/0066088 A1 | 3/2011 | Little | |
| 2011/0082566 A1 | 4/2011 | Herr | |
| 2011/0098615 A1 | 4/2011 | Whalen | |
| 2011/0105966 A1 | 5/2011 | Kazerooni | |
| 2011/0166489 A1 | 7/2011 | Angold | |
| 2011/0257764 A1 | 10/2011 | Herr et al. | |
| 2011/0266323 A1 | 11/2011 | Kazerooni | |
| 2011/0313331 A1 | 12/2011 | Dehez | |
| 2012/0004581 A1 | 1/2012 | Dinon | |
| 2012/0071797 A1 | 3/2012 | Aoki | |
| 2012/0150086 A1 * | 6/2012 | Cohen | A61F 5/0104 |
| | | | 602/27 |
| 2012/0172770 A1 | 7/2012 | Almesfer | |
| 2012/0179075 A1 | 7/2012 | Perry | |
| 2012/0235417 A1 | 9/2012 | Arntz | |
| 2012/0238914 A1 | 9/2012 | Goldfield | |
| 2013/0046218 A1 | 2/2013 | Wiggin | |
| 2013/0237884 A1 | 9/2013 | Kazerooni | |
| 2014/0142475 A1 | 5/2014 | Goldfarb | |

FOREIGN PATENT DOCUMENTS

| | | |
|---|---|---|
| CA | 2731612 | 1/2010 |
| CA | 2724062 | 2/2010 |
| CA | 2734469 | 4/2010 |
| CA | 2740438 | 4/2010 |
| CA | 2746327 | 9/2010 |
| CA | 2769975 | 1/2011 |
| CN | 102164571 | 8/2011 |
| CN | 101938967 | 1/2011 |
| CN | 102036638 | 4/2011 |
| CN | 102065799 | 5/2011 |
| CN | 102088933 | 6/2011 |
| CN | 102098986 | 6/2011 |
| EP | 1842518 A1 | 10/2007 |
| EP | 1260201 | 12/2008 |
| EP | 2231096 | 9/2010 |
| EP | 2296602 | 3/2011 |
| EP | 2326288 | 6/2011 |
| EP | 2331026 | 6/2011 |
| EP | 2346447 | 7/2011 |
| EP | 2349121 | 8/2011 |
| EP | 2373276 | 10/2011 |
| EP | 2448540 | 5/2012 |
| KR | 1020100106527 | 10/2010 |
| WO | 2006078871 A2 | 7/2006 |
| WO | 2006113520 A2 | 10/2006 |
| WO | 2009081710 A1 | 7/2009 |
| WO | 2009143161 | 11/2009 |
| WO | 2009151630 A1 | 12/2009 |
| WO | 2010005473 | 1/2010 |
| WO | 2010011848 | 1/2010 |
| WO | 2010019300 | 2/2010 |
| WO | 2010/025403 A1 | 3/2010 |
| WO | 2010036791 | 4/2010 |
| WO | 2010044087 | 4/2010 |
| WO | 2010101595 | 9/2010 |
| WO | 2011002306 | 1/2011 |
| WO | 2011026086 A1 | 3/2011 |
| WO | 2011/127410 A2 | 10/2011 |
| WO | 2011127421 | 10/2011 |
| WO | 2012027336 | 3/2012 |
| WO | 2012037555 | 3/2012 |
| WO | 2012044621 | 4/2012 |
| WO | 2012048123 | 4/2012 |
| WO | 2012052988 | 4/2012 |
| WO | 2012100250 | 7/2012 |
| WO | 2012125765 A2 | 9/2012 |
| WO | 2012171000 A1 | 12/2012 |

(56) References Cited

FOREIGN PATENT DOCUMENTS

WO          2012177125 A1    12/2012
WO          2013019749 A1     7/2013

OTHER PUBLICATIONS

Extended European Search Report for European Patent Application No. 14826878.2, dated Feb. 7, 2017.

* cited by examiner

TRANSMISSION ASSEMBLY FOR USE IN AN EXOSKELETON APPARATUS

FIELD

This specification relates to an exoskeleton apparatus. In a preferred embodiment, this specification relates to a transmission assembly for an exoskeleton apparatus. Preferably, the transmission assembly imparts rotational motion to a joint along a drive axis that is offset vertically from, and optionally oriented generally parallel to, the axis of movement of the joint.

INTRODUCTION

The following is not an admission that anything discussed below is part of the prior art or part of the common general knowledge of a person skilled in the art.

Spinal cord injury is one of the primary causes of paralysis. Spinal cord injuries can be of varying severity, ranging from high C level injuries to Low S level injuries. Spinal cord injuries may result in paraplegia—the loss of movement or feeling in the lower limbs—or even quadriplegia—the loss of movement or feeling in both the lower and upper limbs.

A person with complete or partial paraplegia is typically restricted to a seated or recumbent position. Aside from the obvious health difficulties, such as lack of mobility, there are numerous secondary health issues associated with paraplegia. Some of the most common secondary conditions include pressure ulcers, respiratory problems, genitourinary problems, spasticity, pain, and autonomic dysreflexia.

Because of all these secondary health complications, rehospitalization for paraplegia patients outpaces the general population by up to 2.6 times normal. Also, secondary conditions do not exist in isolation but have the potential to exacerbate each other, which can lead to serious health complications.

However, if paraplegics are provided with the ability to be in an upright position and mobile, for example using an assistive device, many of these complications can be reduced or eliminated.

Moreover, a suitable assistive device can provide on-going, active rehabilitation, which has the potential to restore motion and feeling in some patients' limbs over time. This is especially so if use of the assistive device is initiated immediately following initial injury.

Currently, rehabilitation is a manual and laborious process. A patient typically must regularly visit a rehabilitation clinic, where a specialist physiotherapist assists the patient through the use of various exercise machines and devices. The patient may also be guided through manual exercise by the physiotherapist. However, once the session is complete, the patient typically returns to a wheelchair and receives no further exercise until the next rehabilitation session.

Various types of exoskeleton apparatus are known that may be used for patients. For example, exoskeletons may be provided for the arms or legs of a user. Where a user has full use of the limb supported by the exoskeleton, the exoskeleton may be used to enhance natural abilities, for example to carry a heavy load. In other cases, where the user has impaired use of the limb supported by the exoskeleton, the exoskeleton may be used for rehabilitative purposes or to replicate full function.

Typically, an exoskeleton for the legs includes a body portion that contacts a user's torso or waist, an upper leg portion moveably mounted to the body portion, and a lower leg portion moveably mounted to the upper leg portion.

Exoskeletons may also be powered, in which case they may have one or more motors coupled to gears or pulleys configured to move the upper and lower leg portions to facilitate the user's desired motion, such as walking.

SUMMARY

This summary is intended to introduce the reader to the more detailed description that follows and not to limit or define any claimed or as yet unclaimed invention. One or more inventions may reside in any combination or sub-combination of the elements or process steps disclosed in any part of this document including its claims and figures.

In accordance with one aspect, which may be used by itself or with any one or more other aspects, the upper limb portion is pivotally mounted to the rest of the exoskeleton about a pivot axis that is vertically offset from the lateral transmission axis of the drive force to the gears of the joint. Improper alignment of the exoskeleton joint may impose stress on a user's joint.

Advantages of the off-set pivot axis in the described designs include having a powered rotational axis of the exoskeleton that is offset from the user's natural joint pivot axis. In the described off-set axis, the joint pivot axis is allowed to freely rotate, while the powered rotational axis is drivenly coupled to the motor output axis. This decoupling of the joint rotational axis and the power transmission rotational axis allows the joint to move in a natural pivot motion, while allowing the exoskeleton to use a more efficient gear assembly for transmitting rotational power.

In accordance with this aspect, there is provided an exoskeleton for a limb of a user wherein the limb has an upper portion connected to the body of a user and a lower limb portion, the upper limb is rotatable to the body about a first axis and the upper and lower limbs are rotatable to each other about a second axis, the exoskeleton comprising:
  (a) a body portion;
  (b) at least one limb structure comprising an upper limb portion and a lower limb portion, wherein the upper limb portion may be pivotally mounted to the body portion about a first limb portion pivot axis or the upper limb portion may be pivotally mounted to the lower limb portion about a second limb portion pivot axis;
  (c) a first drive motor provided on the upper limb portion; and,
  (d) a first drive force transmission mechanism wherein
    (i) the first drive force transmission mechanism drivingly connects the first drive motor to the body portion and the first drive force transmission mechanism comprises a first transfer member extending parallel to the first limb portion pivot axis and offset from the first axis, or
    (ii) the first drive force transmission mechanism drivingly connects the first drive motor to the lower limb portion and the first drive force transmission mechanism comprises a first transfer member extending parallel to the second limb portion pivot axis and offset from the second axis.

In some embodiments, the upper limb portion may be pivotally mounted to the body portion about a first limb portion pivot axis and the upper limb portion may be pivotally mounted to the lower limb portion about a second limb portion pivot axis, the first drive force transmission mechanism drivingly connects the first drive motor to the body portion and the first drive force transmission mechanism comprises a first transfer member extending parallel to the first limb portion pivot axis and offset from the first axis and a second drive force transmission mechanism drivingly connects a second drive motor to the lower limb portion and the second drive force transmission mechanism comprises a second transfer member extending parallel to the second limb portion pivot axis and offset from the second axis.

In some embodiments, the exoskeleton may be configured such that the first limb portion pivot axis may be positioned proximate the first axis or the second limb portion pivot axis may be positioned proximate the second axis.

In some embodiments, the first limb portion pivot axis may be spaced from the first transfer member or the second limb portion pivot axis may be spaced from the first transfer member.

In some embodiments, the drive force transmission mechanism comprises a gear provided on a lower end of the body portion, the gear may be surrounded by a perimeter and the first limb portion pivot axis may be located at a lower portion of the perimeter or the drive force transmission mechanism comprises a gear provided on an upper end of the lower limb portion, the gear may be surrounded by a perimeter and the second limb portion pivot axis may be located at an upper portion of the perimeter.

In some embodiments, a motor axis of the first drive motor may extend generally parallel to the upper limb portion and may be transverse to the first transfer member.

In some embodiments, the first drive force transmission mechanism may be a rotary motion drive force transmission mechanism.

In some embodiments, the first drive force transmission mechanism may comprise a drive gear on a motor output axle, a driven gear on one end of the first transfer member, a drive gear on the other end of the first transfer member and a driven gear provided on the body portion or the lower limb portion.

In some embodiments, the first drive force transmission mechanism may comprise an internal gear provided on a lower end of the body portion or an upper end of the lower limb portion and the internal gear may have a constant arc.

In some embodiments, the internal gear may comprise a stop member associated with one end thereof.

In some embodiments, the internal gear may comprise a stop member associated with each end thereof.

In some embodiments, the internal gear may have a travel portion having an arc of from 30° to 150°.

In some embodiments, the internal gear may have a driven side on which the first transfer member may be provided and an opposed side and the opposed side may be closed.

In some embodiments, the first drive force transmission mechanism may further comprise a drive gear provided on a motor output axle and the drive gear may be drivingly connected to the first transfer member.

In some embodiments, the first transfer member may have a drive gear that may be drivingly connected to a drive gear provided on the lower limb portion or the body portion.

In some embodiments, the first drive force transmission mechanism may comprise an internal gear provided on an upper end of the lower limb portion or a lower end of the body portion, the internal gear may have first and second spaced apart gear ends, the first transfer member may have a drive gear drivingly connected to the internal gear, and the exoskeleton may further comprise a controller operatively connected to the drive motor to prevent rotation of the first transfer member drive gear past the first gear end.

In some embodiments, the internal gear may comprise a first stop associated therewith at the first gear end to stop rotation of the transfer shaft drive prior to or at the first stop.

In some embodiments, the first transfer member may have a driven gear at one end and a drive gear at the other end and at least one of the driven gear and the drive gear may be non-rotatably mounted to the first transfer member by a shearable key.

In some embodiments, the at least one limb structure may comprise a left leg structure and a right leg structure and the body portion comprises a waist member and a plurality of straps securing the user to the leg structures whereby the user's weight is transmitted to the exoskeleton by the left and right leg structures.

In some embodiments, at least one of the straps may comprise an inflatable pocket.

According to another broad aspect, which may be used by itself or with any one or more other aspects, an exoskeleton is provided for facilitating movement of a user's limb or limbs. The exoskeleton comprises a support structure for part or all of a user's limb and a joint. The drive mechanism for the joint utilizes a drive member, which is laterally offset from and has an output drive force member that is at an angle to the direction of transmission of the drive force to the joint. For example, the drive member may be an electrically operate motor with an output shaft. The motor may be mounted on the upper portion of a limb structure (e.g., the portion that extends along the thigh of a user). A drive shaft or other transverse drive member may transmit the rotary drive force from the output shaft transversely to a joint of the exoskeleton. Accordingly, the drive mechanism uses a transmission construction that converts rotary motion about one axis, e.g., a vertical axis in the case of a person walking, to rotary motion about another axis at an angle to the first axis, e.g., a horizontal axis in the case of a person walking.

In some embodiments, the exoskeleton may be configured for a user's legs. In such a case, two symmetrical leg structures may be provided, along with a torso support. The leg structures may be articulable at joints that are aligned with the user's own joints, specifically the hips, knees and ankles. Alternately, or in addition, the exoskeleton may be configured for a user's arms.

Each hip and knee joint may have a transmission construction that transfers rotary drive motion from motors mounted on an upper leg portion to gears within the exoskeleton joints.

One advantage of the transmission construction is that the drive motors may be provided on the upper leg portion, since the upper leg portion is anatomically better suited to support the additional weight as compared to the lower leg. More particularly, if a drive motor were provided on the lower leg below the knee, the lower leg would have a higher mass moment of inertia. This weight reduction reduces stress on the user's knee joint.

A further advantage of mounting the drive motor for the knee on the upper leg portion only, the design of the lower leg portion can be considerably simplified. This simplified construction simplifies the design requirements for the knee joint of the exoskeleton.

Further advantages of the transmission construction include facilitating the mounting of motors with their rotational output axis generally parallel to the longitudinal axis of the upper leg portion. This allows for a more compact design, which allows the user to navigate easily with the aid of crutches. A wider design of the exoskeleton may hinder the user's ability to balance effectively with the aid of crutches throughout the entirety of a walking motion.

In accordance with this aspect, the transmission construction is used to transmit rotational power from the motors to the corresponding, e.g., leg or body, portion. Optionally, the gear assembly can use a series of gears and a transverse transfer shaft to provide a gear reduction to reduce rotational speed while increasing torque. As a result, the gear assembly transmits power from the motor output shaft to the transversely oriented rotational axis of the exoskeleton limbs.

Gears may be mounted to their respective shafts (e.g., motor output axle, transverse transfer shaft) using a shearable key. An advantage of the shearable key is that the key can be chosen to deform or break when a predetermined torque is applied, where that torque is less than is likely to cause injury to the user or damage to the exoskeleton.

In accordance with another aspect, which may be used by itself or with any one or more other aspects, an improved foot portion is provided. The foot portion includes a foot plate hingedly mounted to the lower leg portion and biased by a biasing member, such as a spring, to a first position in which the forward portion of the foot is raised off the ground and the rearward portion of the foot is lowered toward the ground.

When in a standing position, the user's weight and the weight of the exoskeleton overcome the biasing such that the foot plate rests level on the ground. When the leg is raised, the biasing causes the forward portion of the foot to be raised upwardly, which facilitates walking and the avoidance of obstacles.

The use of a passive biasing mechanism, such as a spring, eliminates the need for a powered motor and transmission construction to actuate the foot and ankle. This design is thus both lightweight and relatively simple to construct, again reducing weight and complexity.

In accordance with another aspect, which may be used by itself or with any one or more other aspects, an air bladder strap design may be used. The air bladder strap may be inflated to a predetermined pressure that effectively secures the strap against the user's limb or body. While in use, the inflatable bladder distributes pressure against the limb or body, reducing pressure points and the potential for injury.

The air bladder strap may also be continuously or periodically monitored by a controller and inflated or deflated as needed from a source of pressurized air or fluid.

It will be appreciated by a person skilled in the art that an exoskeleton may embody any one or more of the features contained herein and that the features may be used in any particular combination or sub-combination.

DRAWINGS

The drawings included herewith are for illustrating various examples of articles, methods, and apparatuses of the teaching of the present specification and are not intended to limit the scope of what is taught in any way.

DETAILED DESCRIPTION

Figure 1:
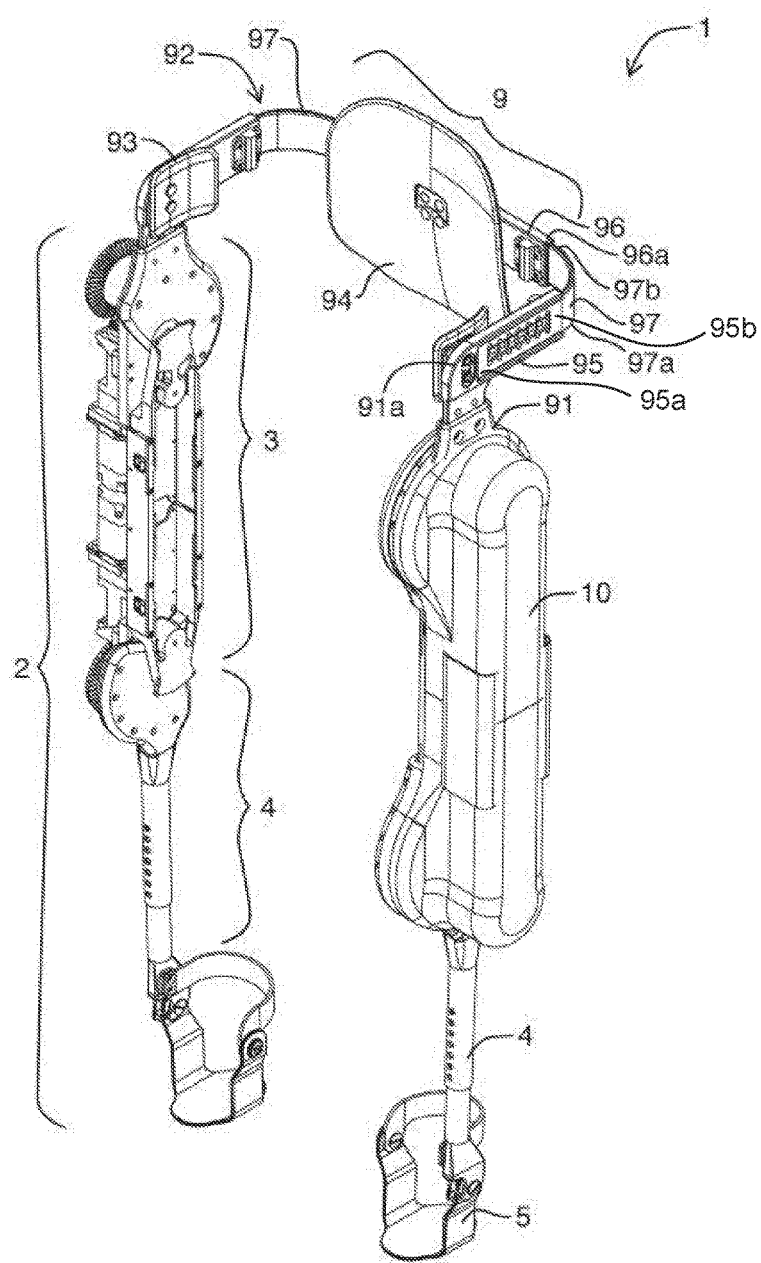
FIG. 1 is a perspective view of an example exoskeleton apparatus with the outer cover of the gear housing cover of one limb removed.
Figure 2:
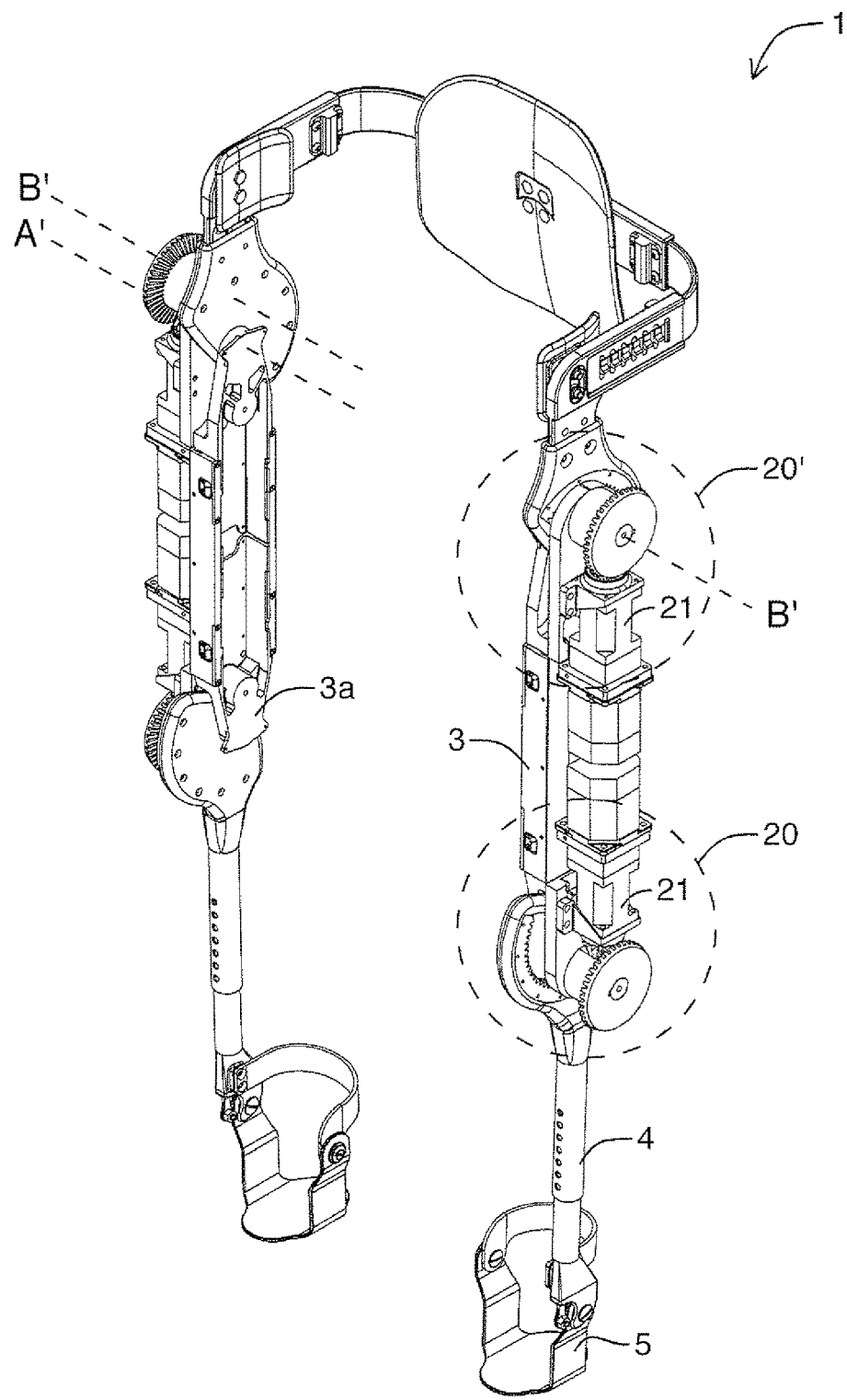
FIG. 2 is a perspective view of the example exoskeleton apparatus of FIG. 1 with the outer cover of the gear housing cover of both limbs removed.
Figure 3:
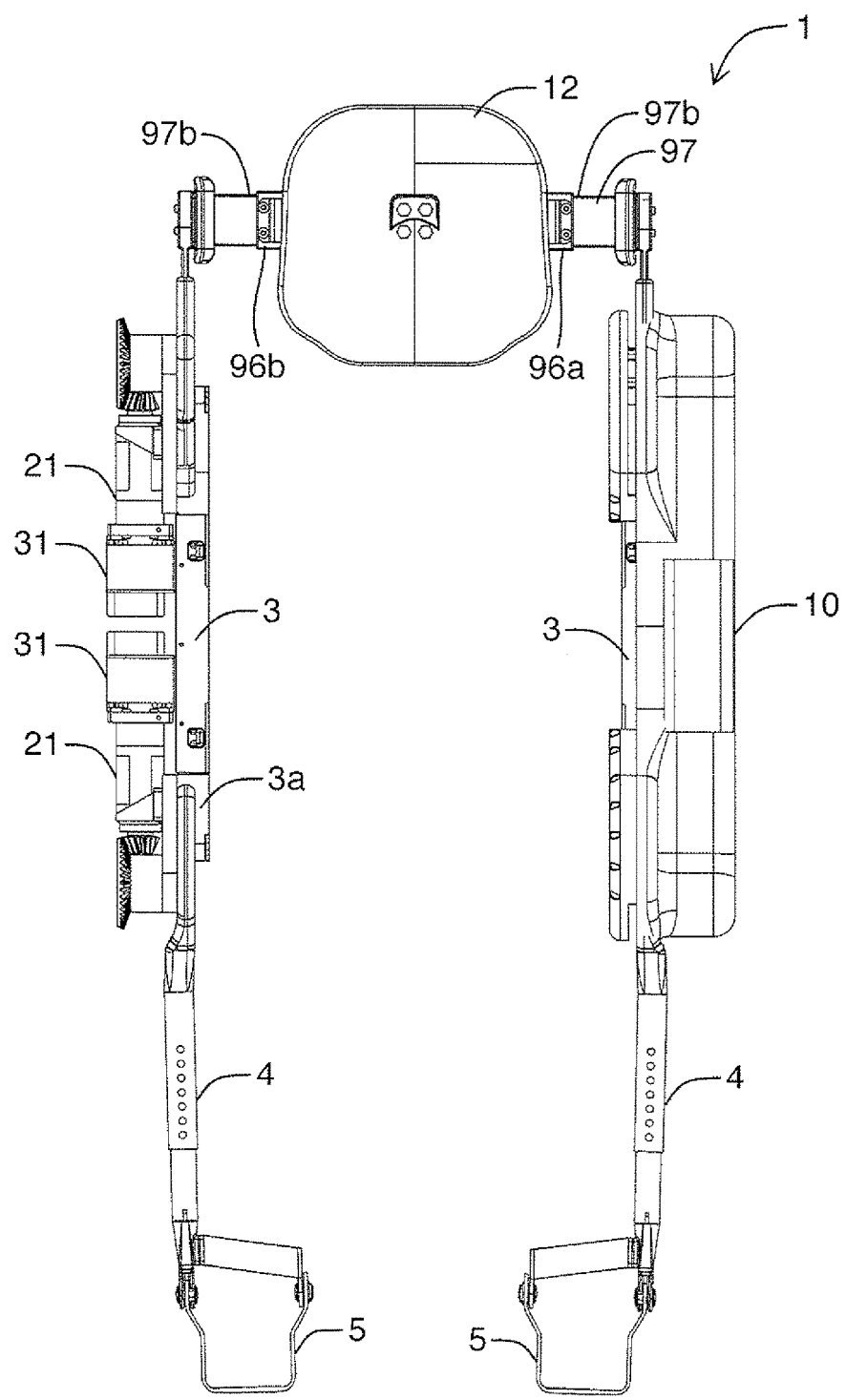
FIG. 3 is a front view of the exoskeleton of FIG. 1.
Figure 4:
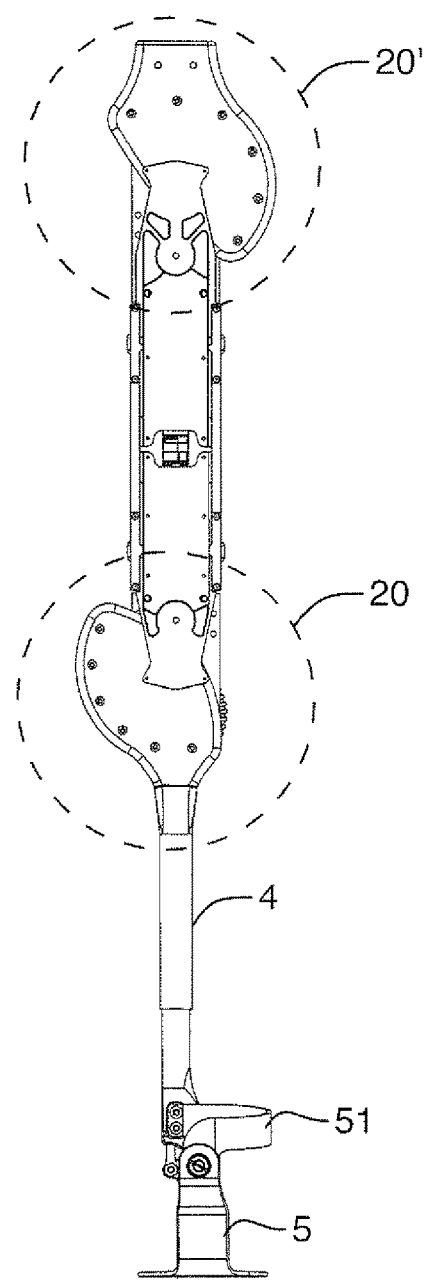
FIG. 4 is an inside side view of a leg structure of the exoskeleton of FIG. 1.
Figure 5:
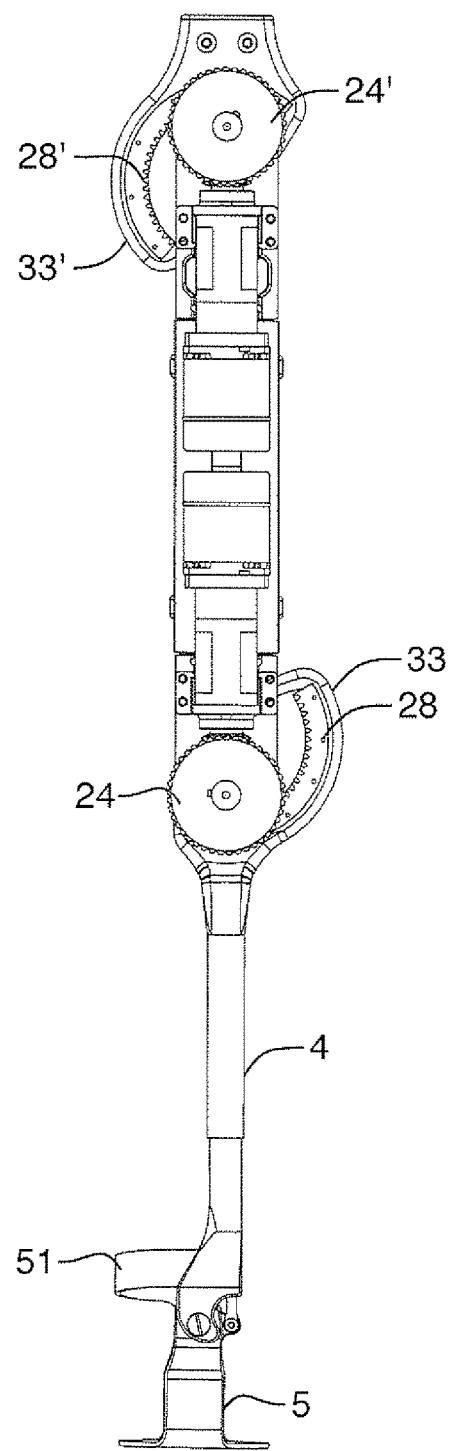
FIG. 5 is an outside side view of the leg structure of FIG. 4 with the gear housing cover removed.
Figure 6:
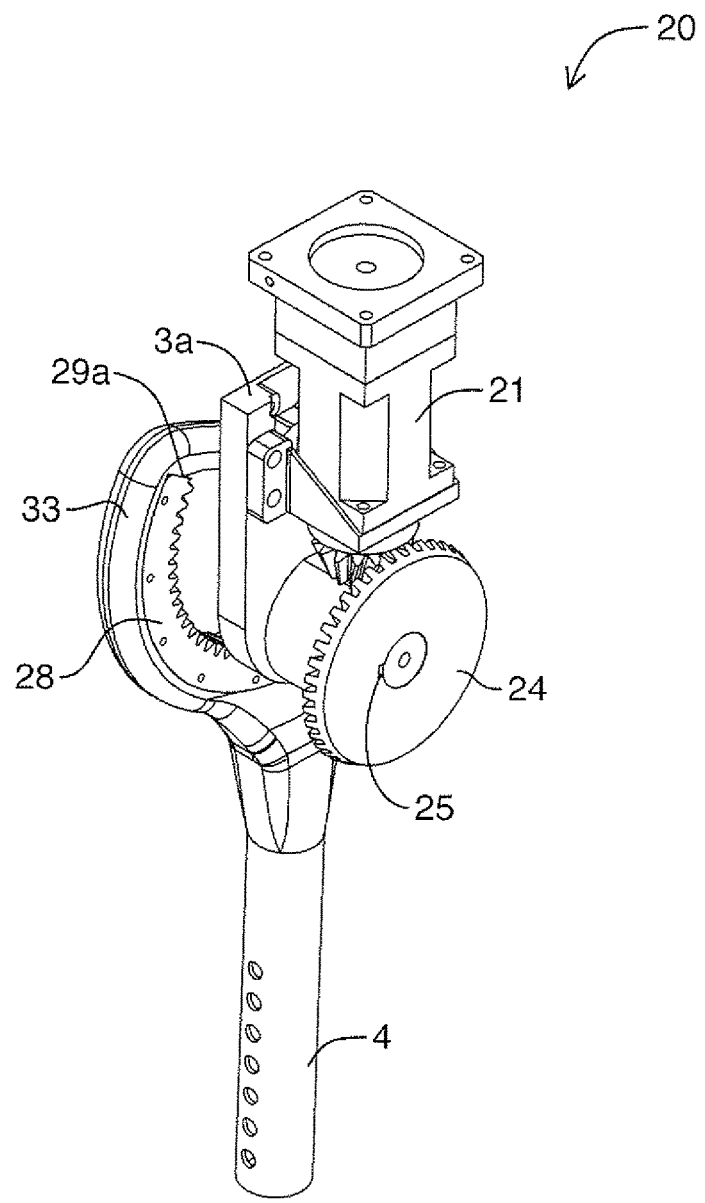
FIG. 6 is a perspective view of an example drive force transmission mechanism for the right leg structure of an exoskeleton.
Figure 7:
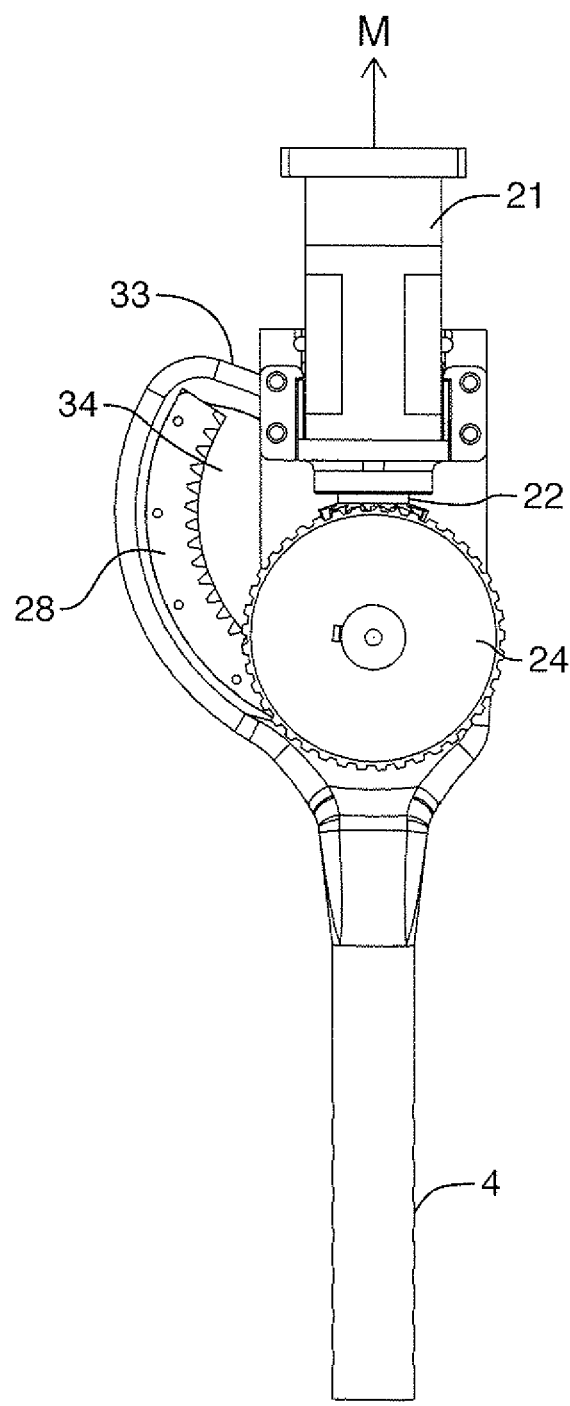
FIG. 7 is a first or outer side view of the drive force transmission mechanism of FIG. 6.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

The described embodiments provide assistive devices suitable for use in supporting and treating paraplegia, by facilitating on-going active rehabilitation. For example, a powered exoskeleton structure is described that supports the patient's legs and torso in an upright position. With the aid of one or more crutches, the patient may stand or walk while using the exoskeleton or may be able to walk just using the exoskeleton. In one embodiment, the exoskeleton may have sensors and a controller that interpret physiological and environmental inputs to allow the patient to, e.g., stand, sit, or walk. For example, physiological inputs may include the angular position of the patient's upper body, balance over both legs, and pressure at the bottom of each foot. Alternately, or in addition if the patient is unbalanced or simply not ready to perform a function, the exoskeleton may remain inactive to avoid injury or unwanted action.

Actuation of the exoskeleton may be provided by electric motors, which may be stepped down with transmissions at each knee or hip joint. In some embodiments, an ankle joint is unpowered, and operates with the aid of a spring-biased mechanism that raises a forward portion of the patient's foot when the rearward portion of the foot is lifted off a walking surface. Power is preferably provided by an on-board battery pack. In other embodiments, a foot plate assembly may not be provided.

The described embodiments are not limited to use by paraplegic patients. Patients with other illnesses or conditions may also benefit from the use of an exoskeleton. For example, patients with middle stage amyotrophic lateral sclerosis (ALS), multiple sclerosis, muscular dystrophy, stroke, or other neurological impairments may benefit from the exoskeleton. Moreover, the exoskeleton may also be beneficial in the treatment of musculoskeletal injuries, such as muscle, tendon or ligament injuries.

It will be appreciated that the exoskeleton may be provided with only one leg structure. For example, a user may only have one limb that has impaired movement or control of movement. It will also be appreciated that the exoskeleton may be designed for a user who has difficulty with the movement of only one joint—such as the hip or the knee. In such a case, the exoskeleton may be configured so as to provide motorized assist for only that joint. It will also be appreciated that the same mechanisms may be used for an exoskeleton that is designed for use with one or both arms of a user. For example, the exoskeleton may have limb structure that is configured to be connected to an arm of a user.

While the described embodiments generally relate to an exoskeleton for the legs of a paraplegic user, an exoskeleton for a quadriplegic user can similarly be provided through the addition of additional joints and motors (e.g., at the hip or waist and at the arms).

General Description of an Exoskeleton Apparatus

Referring to FIGS. 1-5, an example embodiment of exoskeleton 1 is shown. In the embodiment shown, the exoskeleton apparatus is an exoskeleton for both legs of a user. In alternate embodiments, the exoskeleton apparatus may also or alternately include arm and/or upper torso structures (e.g., for a quadriplegic patient), or may be a partial exoskeleton for only one limb or only one joint of one limb.

In the illustrated example, the exoskeleton 1 includes a body portion or support structure 9 that is moveably connected to two limb structures 2. Limb structure 2 comprises an upper limb portion 3 and a lower limb portion 4 and may be configured to support an arm or leg of a user. Upper limb portion may be moveably and drivingly connected both to body portion 9 and a lower limb portion 4. Limb structure 2 may also comprise a foot portion including a foot plate 5, which may be moveably connected to lower limb portion 4. As exemplified, limb structures 2 are of the same construction. However, it will be appreciated that limb structures 2 may differ. It will also be appreciated, for example, that in some embodiments, a lower limb structure may not be required.

Each of upper limb portion 3, lower limb portion 4 and body portion 9 may be formed of a metal, metal alloy, plastic, composite or another suitable material, or combinations thereof. Each portion may be formed of a single contiguous element, or may comprise multiple elements coupled together.

In some embodiments, body portion 9 includes a hip portion 91 and a waist portion 92, which are generally coupled together. Body portion 9 may also have hip rests 93 and a back rest 94 provided thereon for user comfort. Hip rests 93 and back rest 94 may be provided in various suitable configurations. Extruded foam or another suitable material may be used to form the hip and back rests. Alternately, these may be rigid members (e.g., formed of a metal, metal alloy, plastic, composite or another suitable material) which may be padded (e.g., foam or other deformable material). It will be appreciated that the body portion 9 may be used by itself. It will also be appreciated that the different aspects disclosed herein may be used without a body portion 9 or any bory portion known in the art.

In some embodiments, as exemplified in FIG. 1, body portion 9 is configured such that no shoulder harness is provided. Accordingly, weight is not transmitted from the user's upper torso or shoulders to the user's spine. An advantage of this design is that the user may have increased upper body mobility. In addition, the center of gravity of the weight of the exoskeleton experienced by the user will be lower.

Waist portion 92 may be adjustable (e.g., it may be provided with multiple segments) to accommodate users of various body sizes. Accordingly, the elements of waist portion 92 may be rigid members, some or all of which may be moveably connected with respect to adjacent members. As exemplified, waist portion 92 may be provided with a waist adjustment member 95 which has a first end 95a that is securable to hip portion extension 91a at multiple locations and a second end 95b that is securable to a first end 97a of side strap 97 at multiple locations. A waist adjustment member 95 may be provided on each side of the exoskeleton. Alternately, or in addition, waist portion 92 may also be provided with a back adjustment member 96 which has a first end 96a that is securable to second end 97b of side strap 97 at multiple locations and a second end 96b that is securable to the second end 97b of the side strap 97 on the other side of the exoskeleton at multiple locations. In the illustrated example, waist portion 92 includes several segments that are slidably mated to each other. Multiple holes are provided within the segments, allowing for the waist portion to be adjusted to a desired width and depth. Bolts or other suitable fasteners (e.g., a wing nut) may be provided to fix the waist portion at the desired size. Other sileable or connection mechanisms with multiple connection positions may be used. Accordingly, it will be appreciated that waist portion may be of various constructions that permit the waist portion to be adjusted to the size of a particular user.

Preferably, as exemplified, and particularly with an exoskeleton for use with one or more legs of a user, no shoulder strap or other mechanism is provided. Accordingly, the upper torso of a user does not support any weight of the exoskeleton. In an embodiment wherein a foot plate is provided, the exoskeleton essentially supports its own weight. Accordingly, waist portion 92 may be configured to secure or assist in securing the upper portion of the exoskeleton to the lower torso of the user so it is essentially fixed in relative position to the user during use.

In some embodiments, upper limb portion 3 may provide a support structure upon which one or more motors 21 are provided. Preferably, a motor is provided for each joint that is motorized. Preferably, the motors for the joint of the upper limb and the body and the joint of the upper and lower limb are each provided on the upper limb.

An onboard energy storage member may be provided to provide power for the motors. Any energy storage member may be provided and the energy storage member may be provided at any location on the exoskeleton or it may be remotely positioned to the exoskeleton. For example, a power pack may be carried by a user and may have a cord that plugs into the exoskeleton. The energy storage member may comprise one or more batteries. As exemplified in FIG. 3, batteries 31 may be provided on the upper limb portion 3. In other embodiments, one or more batteries 31 may be provided on the body portion 9. It will be appreciated that, as exemplified, each motor may be provided with its own battery. An advantage of this design is that the weight of the batteries is more evenly distributed. Alternately, a central power pack may be provided which is connected to each motor.

The provision of elements such as motors 21 and batteries 31 on the upper limb portion 3, which is closer to the torso of the user, allows the lower limb portion 4 to be lighter, reducing its mass moment of inertia. Reducing the moment of inertia correspondingly reduces the stress on a user's joints (e.g., knee) that would otherwise result from a heavier lower limb portion.

Upper limb portion 3 may be formed of a single contiguous segment, or may be adjustable in length. For example, in some embodiments, upper limb portion 3 may comprise two end segments coupled by a bracket. For example, they may be telescoping elements or comprise side by side members or brackets. By using an alternate bracket that has a different length, or by connecting the brackets together at different locations (e.g., selecting between differently spaced screw holes in the bracket or end segments), the upper limb portion 3 may be lengthened or shortened to accommodate each user. It will be appreciated that any adjustable segment may be used.

If upper limb portion is drivingly connected to the exoskeleton, then each end of upper limb portion 3 may have a mount and a drive force transmission mechanism 20 may be provided to drivingly connect a motor 21 to an adjacent portion of the exoskeleton on the other side of a joint. For example, the upper end of upper limb portion 3 may have a drive force transmission mechanism 20 to drivingly connect a motor 21 to the upper body portion 9 and the lower end of upper limb portion 3 may have a drive force transmission mechanism 20 to drivingly connect a motor 21 to the lower limb portion 4. Preferably, the portions of the exoskeleton are pivotally connected together. Accordingly, as shown in the illustrated embodiments, the mount comprises a pivot 30 having a pivot axis A, as shown in greater detail in FIG. 8.

Pivot 30 may comprise a suitable bearing to facilitate rotational motion of lower limb portion 4 relative to upper limb portion 3 about pivot axis A.

Lower limb portion 4 may be formed of a single contiguous segment, or may be adjustable in length. For example, in some embodiments, lower limb portion 4 may include a telescoping tube structure as illustrated with a plurality of locking positions, and may be lengthened or shortened to accommodate each user. It will be appreciated that lower limb portion may use the same length adjustment mechanism as upper limb portion 3, or it may use a different length adjustment mechanism.

An upper limb cover 10 may be provided to shield portions of exoskeleton 1 from dust and other contaminants, and also to protect moving elements of exoskeleton 1 from external objects. Upper limb cover 10 may be formed of a metal, metal alloy, plastic, composite or another suitable material.

Transmission Construction

In accordance with one aspect of the teachings described herein, the following is a description of a transmission or gear construction, which may be used by itself in any exoskeleton or in any combination or sub-combination with any one or more other aspects disclosed herein including the offset pivot axis construction, the foot plate assembly construction and the air bladder strap construction. Generally, the drive force transmission mechanism 20 is configured to transmit drive force between a motor provided on the upper limb portion and the body portion, and/or between a motor on the upper limb portion and the lower limb portion. Accordingly, in combination, the motor and the drive force transmission mechanism provide a powered joint. In accordance with this aspect, drive force transmission mechanism 20 adapts a rotational force from a motor mounted on the upper limb portion and having a motor axis that is generally parallel to the limb, and transmits it laterally via one or more gears to the body portion or lower limb portion.

An advantage of aligning the output axle of the motor transverse to the transmission direction of the motor to the joint, is that the motor having a lower torque level may be provided and accordingly, a smaller motor may be used. The use of a smaller motor will enable the use of a lighter motor and, using the same on board energy source, a longer operating life may be obtained.

A further advantage of aligning the output axle of the motor transverse to the transmission direction of the motor to the joint is that the profile of the limb structure may be reduced. If the motor axis was aligned with the axis of rotation of the gears, then the motor would extend further outwardly, and increase the clearance that would be required for a user to avoid walls, furniture and the like.

Referring to FIGS. 6-17, an example embodiment of a drive force transmission mechanism 20 is shown for use in an exoskeleton, such as exoskeleton 1, for at least one limb structure corresponding to a limb of a user. FIGS. 6-11 illustrate the complete transmission mechanism 20 along with sub-portions of the upper and lower limb portions. FIGS. 12-17 illustrate a partial drive force transmission mechanism 20, in which selected parts have been omitted to provide a better view of internal components.

Generally, the at least one limb structure may have an upper portion or upper limb portion 3, connected to the body portion 9, or lower limb portion 4, or both. The upper limb portion 3 may be moveably mounted to the body portion 9 and lower limb portion 4 may be moveably mounted to the upper limb portion 3. In at least some embodiments, upper limb portion 3 is pivotally moveably mounted to the body portion 9 and lower limb portion 4 is pivotally moveably mounted to the upper limb portion 3

In the example shown, exoskeleton 1 has a left leg structure and a right leg structure, and a waist member or body portion 9. The exoskeleton may be secured to the user by any means known in the art. Preferably, a plurality of straps may also be provided at various positions on the exoskeleton. For example, straps may be provided for securing the user to the leg structures to thereby transmit the user's weight to the exoskeleton by the left and right leg structures. A waist strap may also be provided to secure the exoskeleton to the lower torso of a user. In some embodiments, the straps may include at least one inflatable pocket to enhance comfort and to distribute pressure on the user's limbs or torso.

In accordance with this aspect, a drive motor 21 may be provided on the upper limb portion 3. Drive motor 21 has a motor axis M that extends generally parallel to the upper limb portion 3. More particularly, drive motor 21 is oriented such that the motor output axle 22 is generally parallel to the longitudinal axis of upper limb portion 3. This facilitates a compact and efficient arrangement of elements on the exoskeleton 1.

Drive motor 21 may be mounted to or proximate upper limb portion end 3a or output axle 22 may have a sufficient length such that drive gear 23 is positioned to drivingly engage driven gear 24.

In some embodiments, drive motor 21 may incorporate, or be coupled to, a planetary gear box to decrease the output speed of a motor output axle 22 while increasing its torque.

In the illustrated example of FIGS. 6-17, the drive force transmission mechanism 20 shown is a rotary motion drive force transmission mechanism used to drivingly connect the drive motor 21 to the lower limb portion 4 of exoskeleton 1 (e.g., at a knee joint). More particularly, lower limb portion 4 is moveably mounted and, preferably, pivotally mounted to upper limb portion 3.

Drive force transmission mechanism 20 comprises a first gear or driven gear 28 provided on an upper end of the lower limb portion 4. The driven gear 28 may be any gear coupled to the lower limb portion 4. The gear may be an internal gear. It is preferred that the gear has a constant arc, and may provide a travel distance of between 10-150° or between 30-150°. The travel distance may vary depending upon the joint and is preferably selected to permit a normal range of motion of the joint (preferably while walking and moving into and out of a sitting position).

Drive force transmission mechanism 20 further comprises a first transfer member extending transverse to the motor axis M.

In some embodiments, the first transfer member may comprise a single transverse gear, e. g., a gear to transfer the rotary output from the drive motor transverse or laterally to the lower limb portion. For example, drive gear 23 provided on the motor output axle 22 may drivingly engage such a transverse gear and the transverse gear may directly drivingly engage driven gear 28. Alternately, drive gear 23 may directly drivingly engage driven gear 28 or an extension thereof. However, in other embodiments, including the example shown, the transfer member comprises a transfer shaft 26, which has a drive gear 27 provided thereon at a first end, and a driven gear 24 provided thereon at a second opposing end. The drive gear 27 is drivingly connected to the driven gear 28. One or both of drive gear 27 and driven gear 28 may be helical gears, while in other embodiments they may be spur gears or other suitable gear. Helical gears offer the advantage of quieter operation relative to spur gears.

Driven gear 24 is driven by a drive gear 23 provided on the motor output axle 22, which is mounted transversely to transfer shaft 26. In the illustrated example, drive gear 23 and driven gear 24 are bevel gears. Drive gear 23 is non-rotatably mounted to motor output axle 22, for example using a shearable key. Drive gear 23 may be a bevel gear for drivingly coupling with a driven gear 24, which is also beveled. In other embodiments, drive gear 23 may be drivingly coupled to driven gear 24 using other configurations, such as a worm gear.

To prevent injury to the user from over-torque conditions, at least one of the gears, and preferably one of the driven gear 24 and drive gear 27 is shearably mounted to transfer shaft 26, e.g., it may be non-rotatably mounted to transfer shaft 26 using a shearable key 25. Similarly, drive gear 23 may be non-rotatably mounted to motor output axle 22 using a shearable key. The shearable keys can be formed of a material, such as a soft metal alloy, that deforms and shears when a predetermined force is applied, where the predetermined force is selected to be lower than is likely to cause injury to the user, or damage to exoskeleton components, or both.

In some embodiments, the drive force transmission mechanism provides a gear reduction of from 1:200 to 1:600. In some embodiments, the drive force transmission mechanism provides a gear reduction of from 1:300 to 1:500.

In some embodiments, driven gear 28 is an internal gear (i.e., the gear teeth are provided on an interior side and not an exterior side). It will be appreciated that an internal gear may extend in a full circle and may have teeth on part or all of the inner surface. Alternately, as exemplified, internal gear 28 is constructed as an arc. In such an embodiment, a gear housing 33 may be provided at an end of the lower limb portion 4, to surround an outer portion of driven gear 28 and preferably to close the open end of an arc shaped drive gear 28 so as to define an enclosed interior space 34 (see FIG. 11). Accordingly, the internal driven gear 28 has a driven side with teeth which are engaged by the teeth of drive gear 27 on transfer shaft 26 and an opposed side which may be closed by the gear housing 33.

As shown, driven gear 28 may be an internal gear and it may be constructed in several manners. For example, it may be formed as part of gear housing 33 (e.g., an integrally formed unit), or driven gear 28 may be fastened to or within gear housing 33. The gear housing may be provided with a back plate 35 that closes the lateral side of opening 34 opposed to that of transfer shaft 26. The gear housing 33 and back plate 35 protect the internal gear from becoming entangled with articles of the user's clothing, or from other external environmental elements. Driven gear 28 may be formed as port of the upper end of lower limb portion 4 or it may be manufactured separately and then attached thereto.

In order to prevent over-rotation of the joint, which could damage a limb of the user, a mechanism may be provided to inhibit or prevent rotation of the joint past a predetermined limit. The limit may be set slightly short of the degree of rotation at which the joint of a user may be damaged from over-rotation. For example, driven gear 28 may have first and second spaced apart gear ends 28a and 28b and a stop member 29a or 29b may be provided proximate to one or both spaced apart ends 28a and 28b of driven gear 28 to stop rotation of the transfer member prior to or at the stop. In some embodiments, the stop member 29a or 29b may be part of or integral to gear housing 33. The stop member 29a or 29b may be of any construction and may be provided on any part so as to be engaged by, e.g., drive gear 27 and prevent rotation of drive gear past the stop. If a shearable connector is provided, then the shearable connector may be sheared upon such an occurrence, thereby preventing damage to the joint of the user and the exoskeleton. It will be appreciated that the stop may be designed to provide resistance to rotation so as to cause the shearable connector to shear.

Alternately, or in addition, the mechanism may comprise a controller operatively connected to drive motor 21 which may be configured to prevent rotation of drive gear 27 past one or both the gear ends 28a and 28b.

Likewise and in similar fashion, a second drive force transmission mechanism 20' may be provided at a hip joint, and may comprise a second transfer member extending transverse to a motor axis of a second drive motor, where the second drive force transmission mechanism 20' drivingly connects the second drive motor to the body portion 9. As exemplified in FIGS. 1-5, upper limb portion 3 is moveably mounted and, preferably, pivotally mounted to body portion 9. In this embodiment, the first gear or driven gear 28 is preferably provided on the body portion 9. For example, driven gear 28 may be provided on the hip portion 91 of body portion 9. In addition, in some embodiments, a gear housing 33 may be provided at an end of the body portion 9.

Accordingly, in some embodiments, the exoskeleton may have two limb structures, one for each leg. As exemplified in FIG. 1, the exoskeleton has a limb structure for the left leg and a limb structure for the right leg. The limb structures are connected to a waist member. The upper limb portion is provided with two motors, one for actuation of the hip joint and one for actuation of the knee joint. One advantage of this design is that sensory receptors are not required in the knee to simulate motor nerves and create a limitation in the range of motion of the knee to protect the cartilage and ligaments associated with the knee of a user from being over rotated.

Another advantage is that the weight of the lower limb portion 4 is reduced and this reduces the forces that are transmitted through the knee joint.

A further advantage is that the lower limb portion 4 may be easier to remove and service or replace. For example, control wiring for a motor need not extend through the knee joint. Further, the lower limb portion may be removable by removing the screws or the like which moveably secure the lower limb portion 4 to the upper limb portion 3 and optionally disengaging the gear on the lower limb portion 4 from the drive force transmission mechanism.

A further advantage is that, by keeping the motors on the upper limb portion 3, and supporting weight by the waist member and/or the upper and lower limb portions, the weight that is transmitted through the ankle joint of the exoskeleton may be reduced thereby the foot plate to be lighter.

Off-Set Pivot Axis

In accordance with another aspect of the teachings described herein, the following is a description of an offset pivot axis, which may be used by itself in any exoskeleton or in any combination or sub-combination with any one or more other aspects disclosed herein, including the transmission construction, the foot plate assembly construction and the air bladder strap construction. Preferably, this construction is used together with the transmission construction.

In accordance with this aspect, the upper limb is pivotally mounted to the lower limb (and/or the body portion) at a position that is vertically spaced from the drive axis of the joint. For example, if the joint uses the transmission construction disclosed herein, then the pivot axis of the joint of the exoskeleton may be vertically offset from the axis of transfer shaft 26. Therefore, the pivot axis of the upper and lower limbs 3, 4 may be above the axis of the transfer shaft 26 for that joint. Similarly, the pivot axis of the upper limbs 3 and the body 9 may be below the axis of the transfer shaft 26 for that joint. It will be appreciated that the pivot axis of the joint of the exoskeleton is preferably proximate the pivot axis of the joint of the limb of the user and preferable located essentially at the joint of the limb of the user.

An advantage of this design is that it allows the drive mechanism at the joint to be sized relatively independently of the constraints imposed by the user's joint. For example, a larger transfer member or gear construction could be used even where it would have a rotational axis that does not align well with the user's own joint. The design may also facilitate increased adjustability for differently sized limbs.

Figure 8:
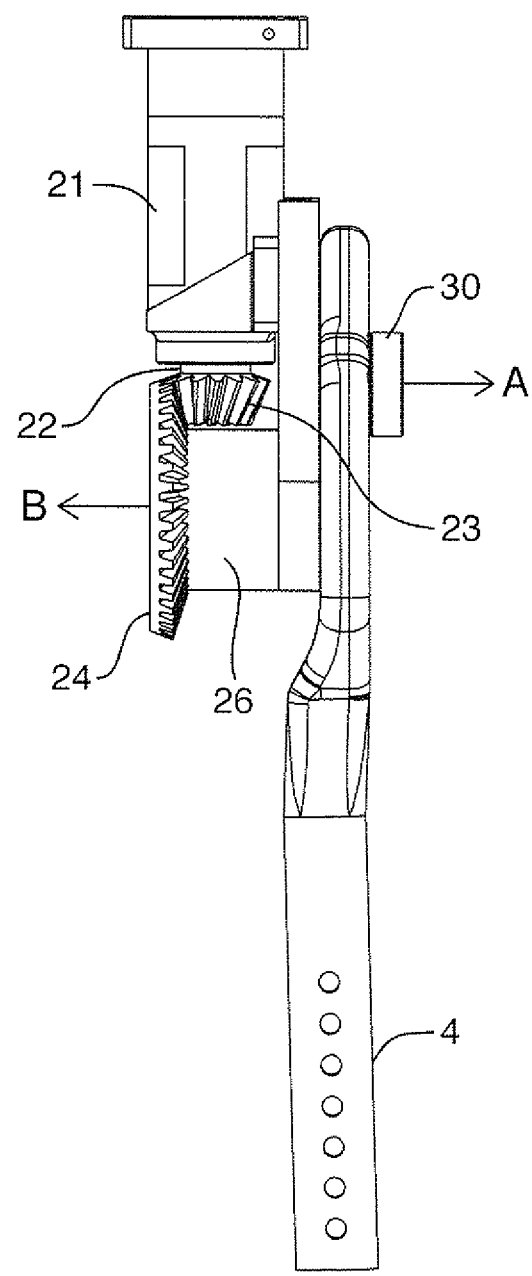
FIG. 8 is a front view of the drive force transmission mechanism of FIG. 6.
Figure 9:
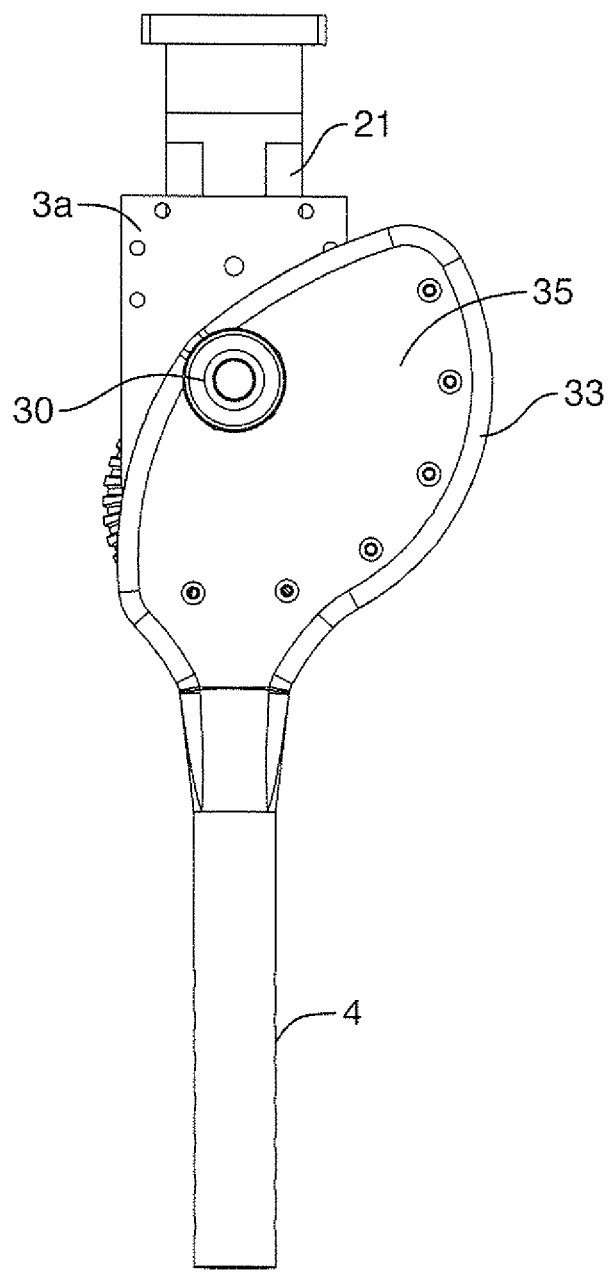
FIG. 9 is a second or inner side view of the drive force transmission mechanism of FIG. 6.
Figure 10:
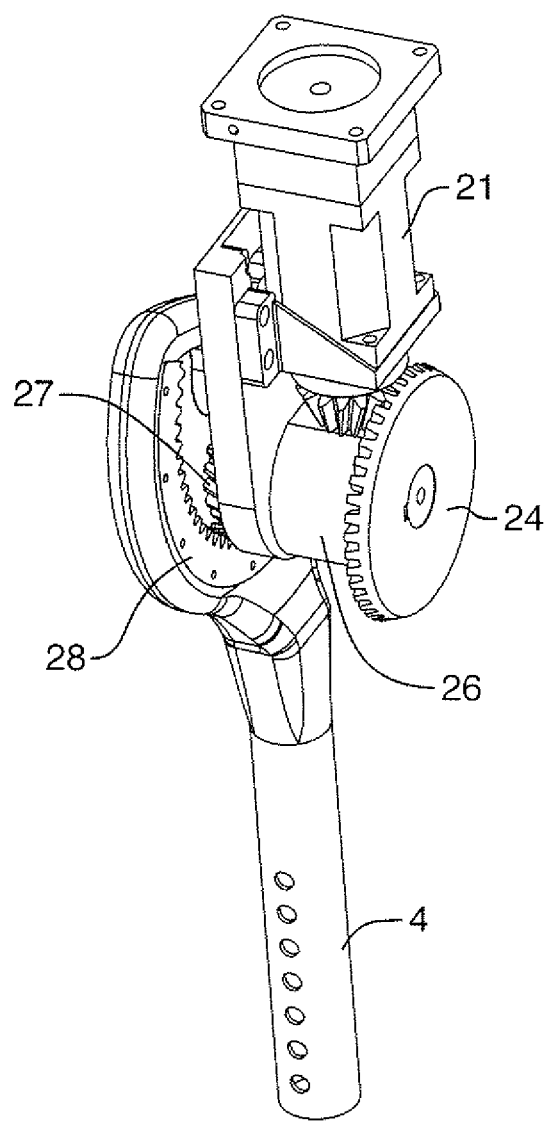
FIG. 10 is a perspective view of an example drive force transmission mechanism for the left leg structure of an exoskeleton.
Figure 11:
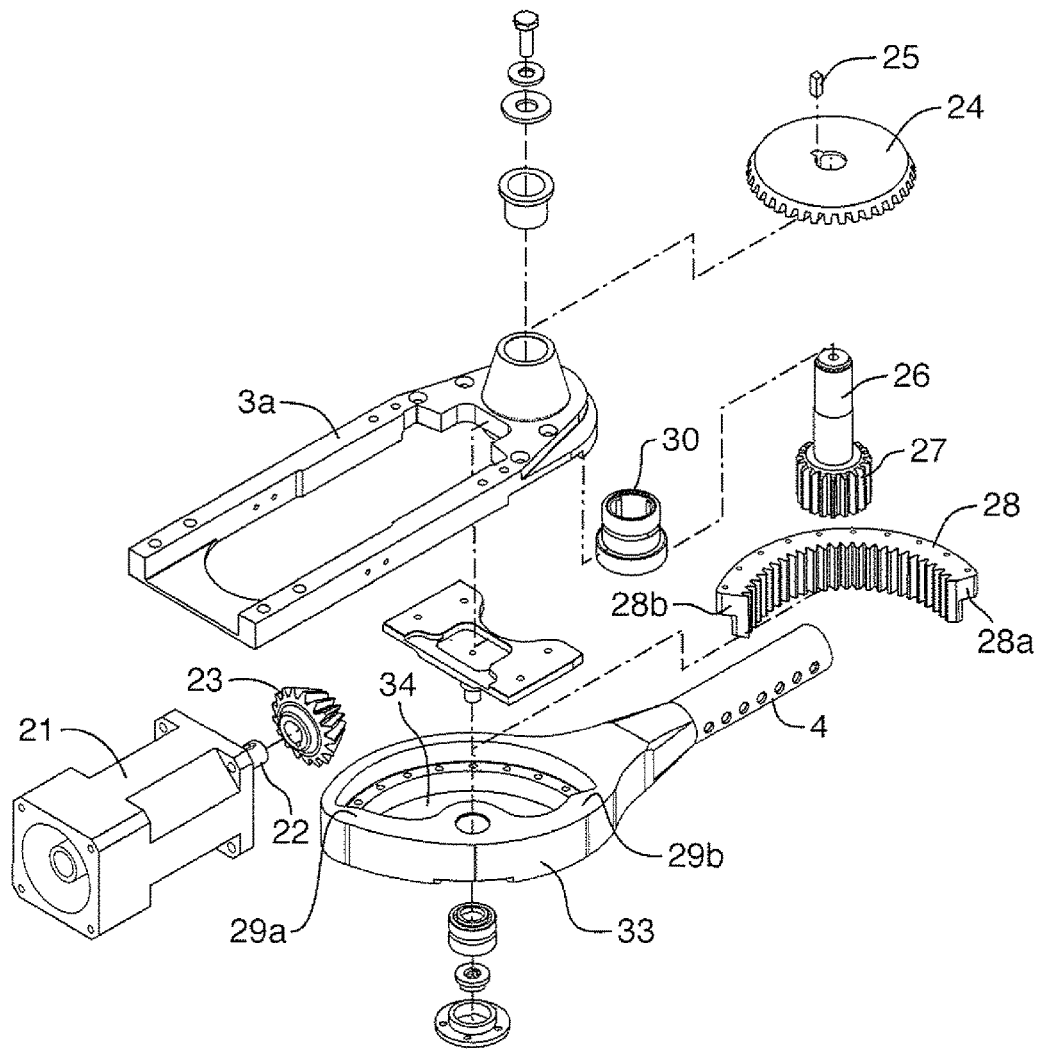
FIG. 11 is an exploded perspective view of the example drive force transmission mechanism of FIG. 6.

In the illustrated example, lower limb portion 4 is pivotally mounted to the upper limb portion 3 about a limb portion pivot axis A (see FIG. 8). Limb portion pivot axis A may be located at any location that extends through a portion of lower limb 4 or an extension thereof, such as drive gear 28 and the associated housing 33, 35. As exemplified, limb portion pivot axis A may be located generally within and at an upper end of housing 33 that surrounds driven gear 28. Pivot axis A may be centered on a bearing 30 that pivotally moveably couples an upper end of lower limb portion 4, such as housing 33, to a lower end of upper leg portion 3, such as upper limb portion end 3a (se FIG. 6).

Figure 12:
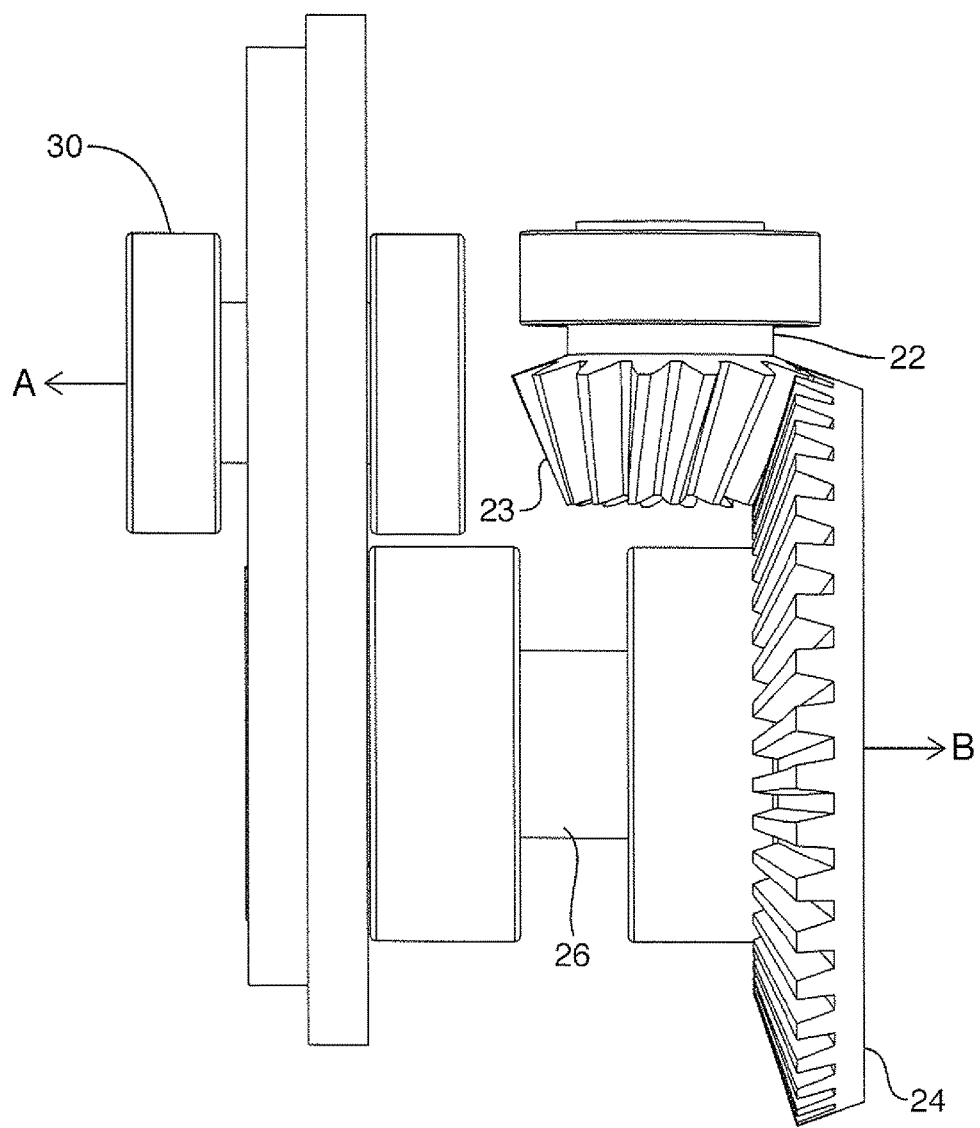
FIG. 12 is a partial enlarged front view of the drive force transmission mechanism of FIG. 6, wherein the drive motor has been removed.
Figure 13:
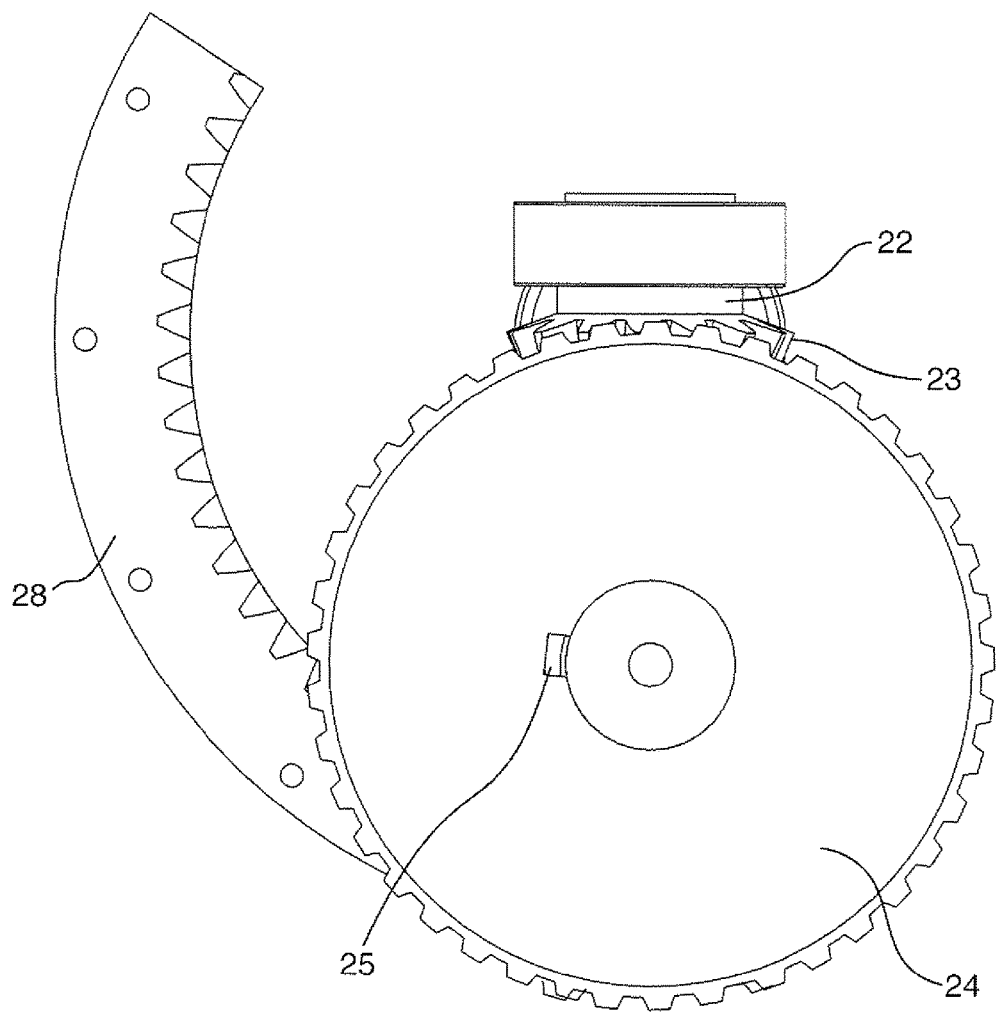
FIG. 13 is an outside side view of the partial drive force transmission mechanism of FIG. 12.
Figure 14:
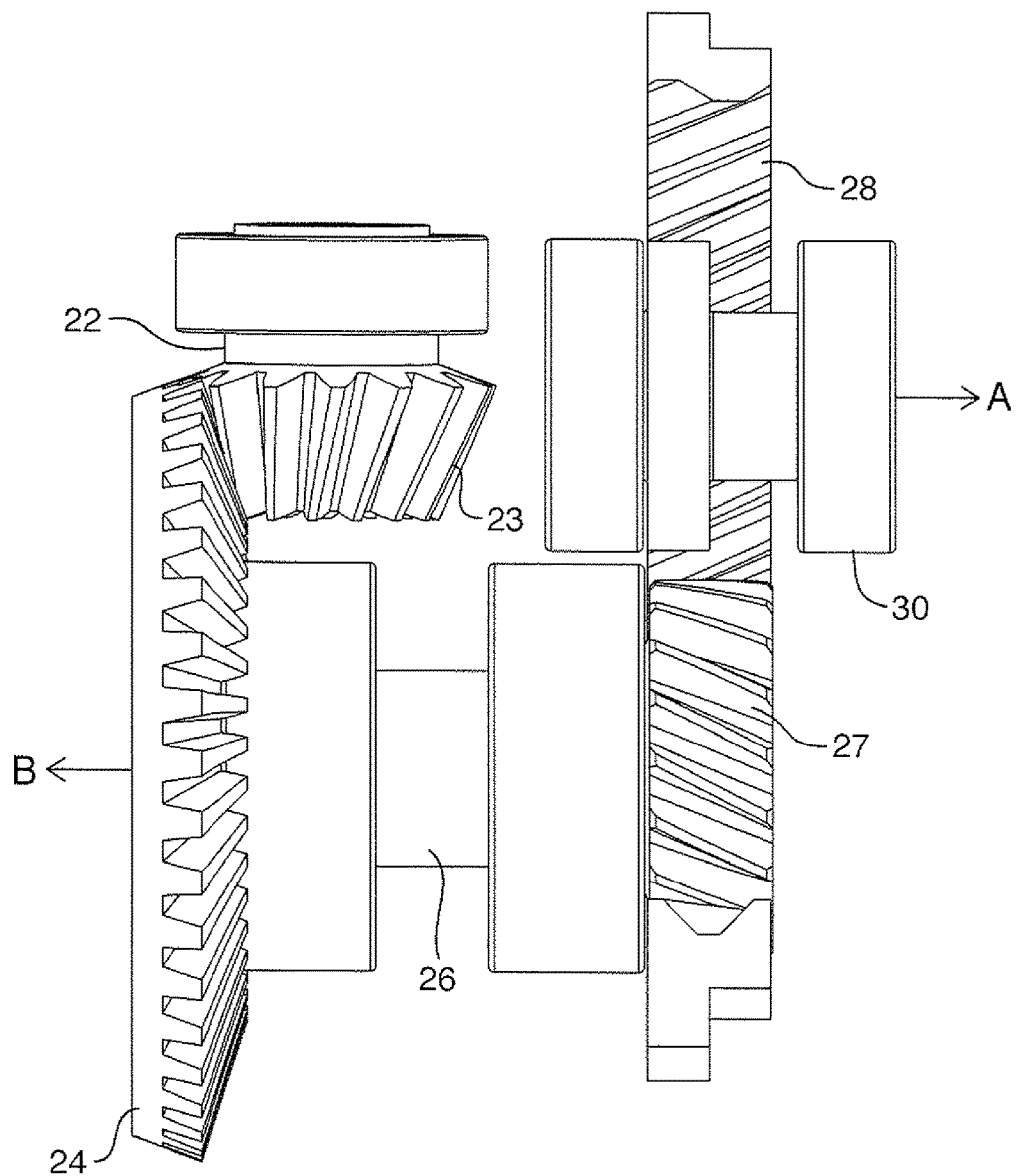
FIG. 14 is a rear view of the partial drive force transmission mechanism of FIG. 12.
Figure 15:
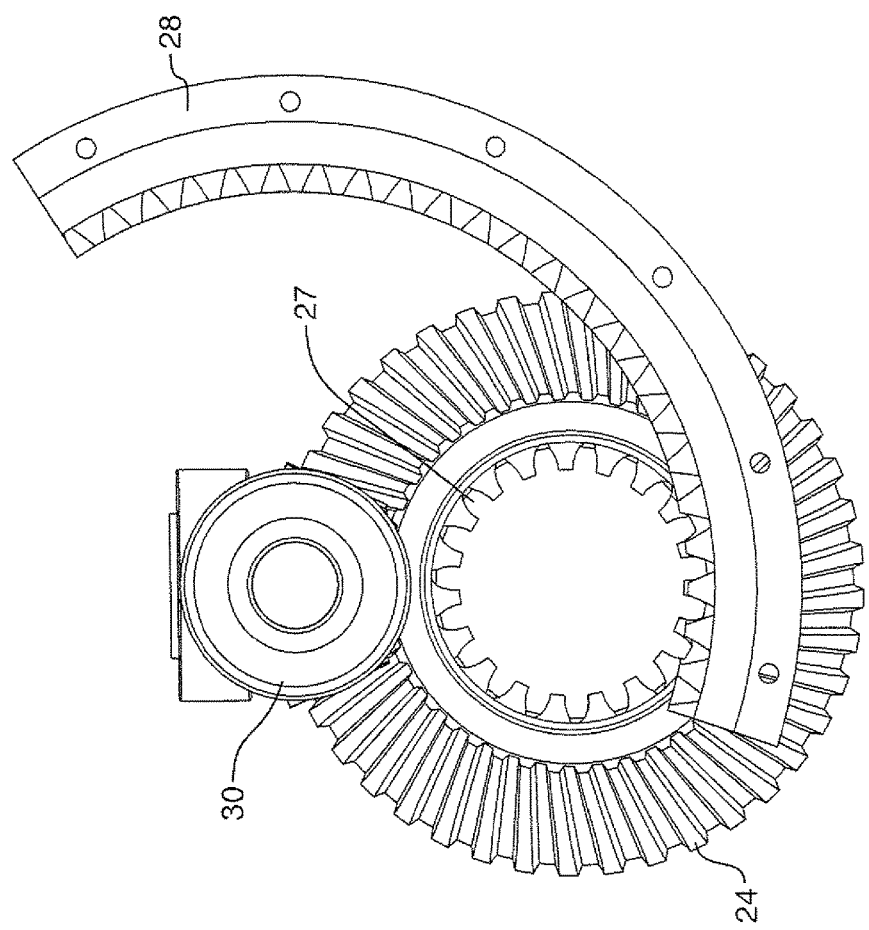
FIG. 15 is an inside side view of the partial drive force transmission mechanism of FIG. 12.
Figure 16:
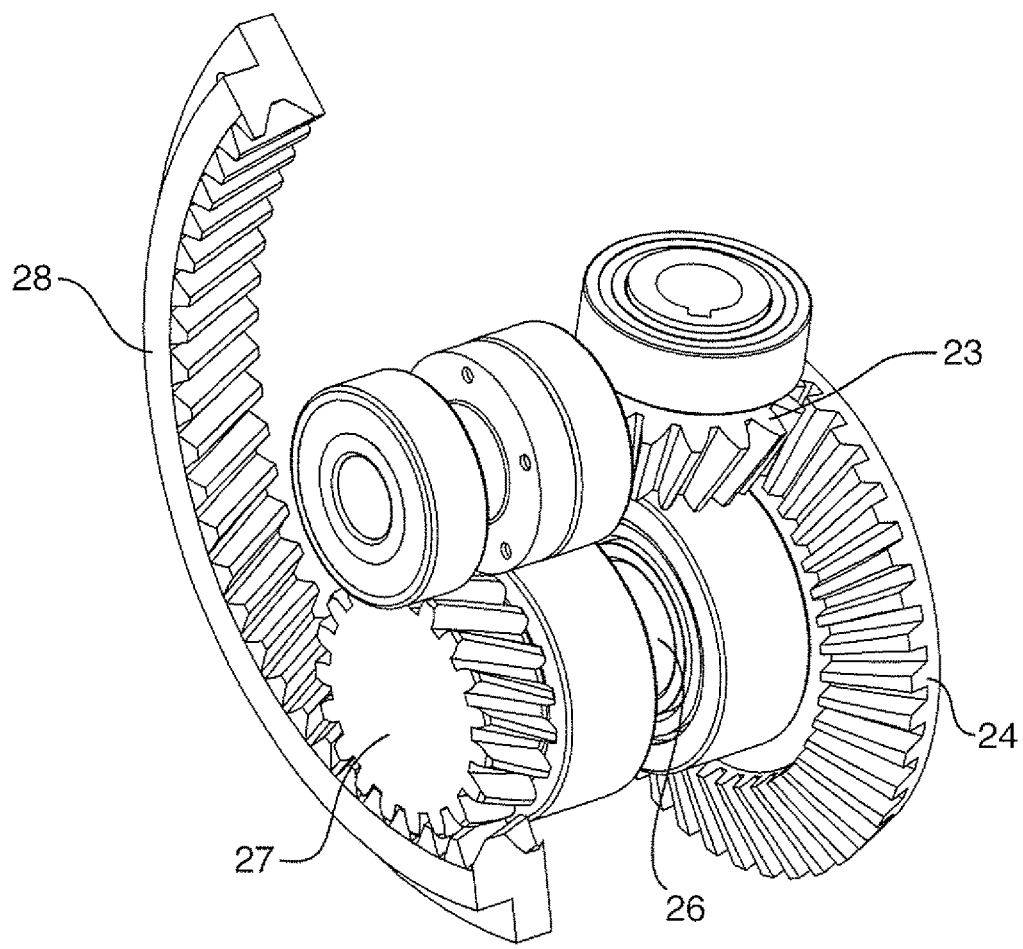
FIG. 16 is a perspective view from the inside of the partial drive force transmission mechanism of FIG. 12 with the drive components outwards of the internal gear removed.
Figure 17:
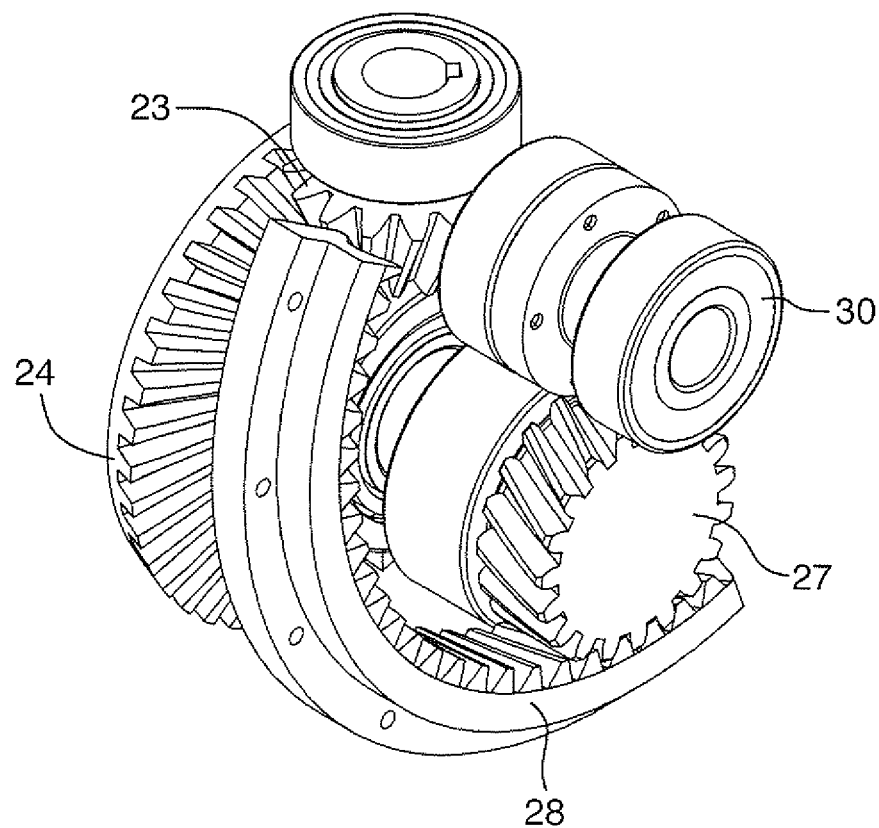
FIG. 17 is a perspective view from the inside of a partial drive force transmission mechanism for the left leg structure of an exoskeleton.
Figure 18:
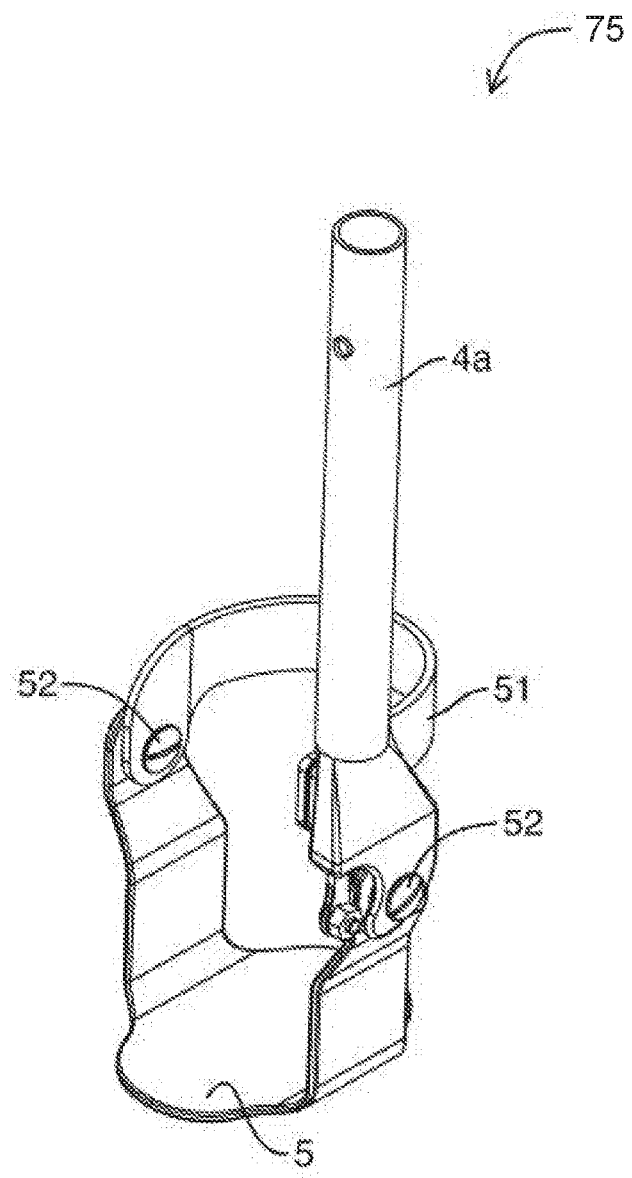
FIG. 18 is a perspective view of a foot portion for the left leg structure of an exoskeleton.
Figure 19:
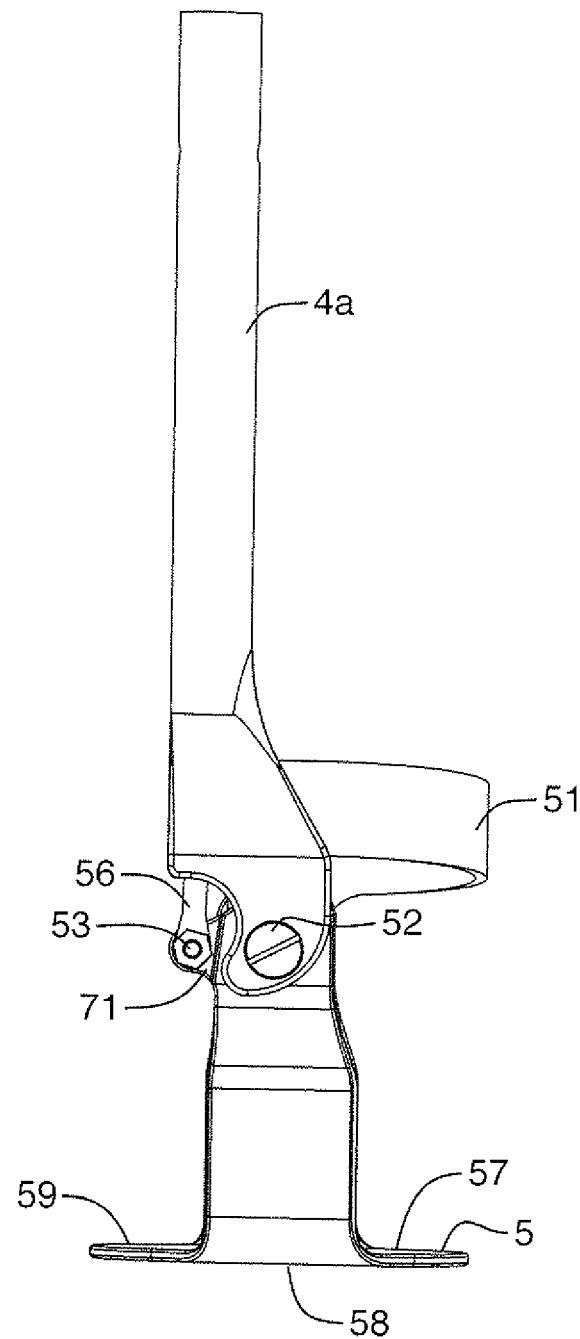
FIG. 19 is an outside side view of the foot portion of FIG. 18.
Figure 20:
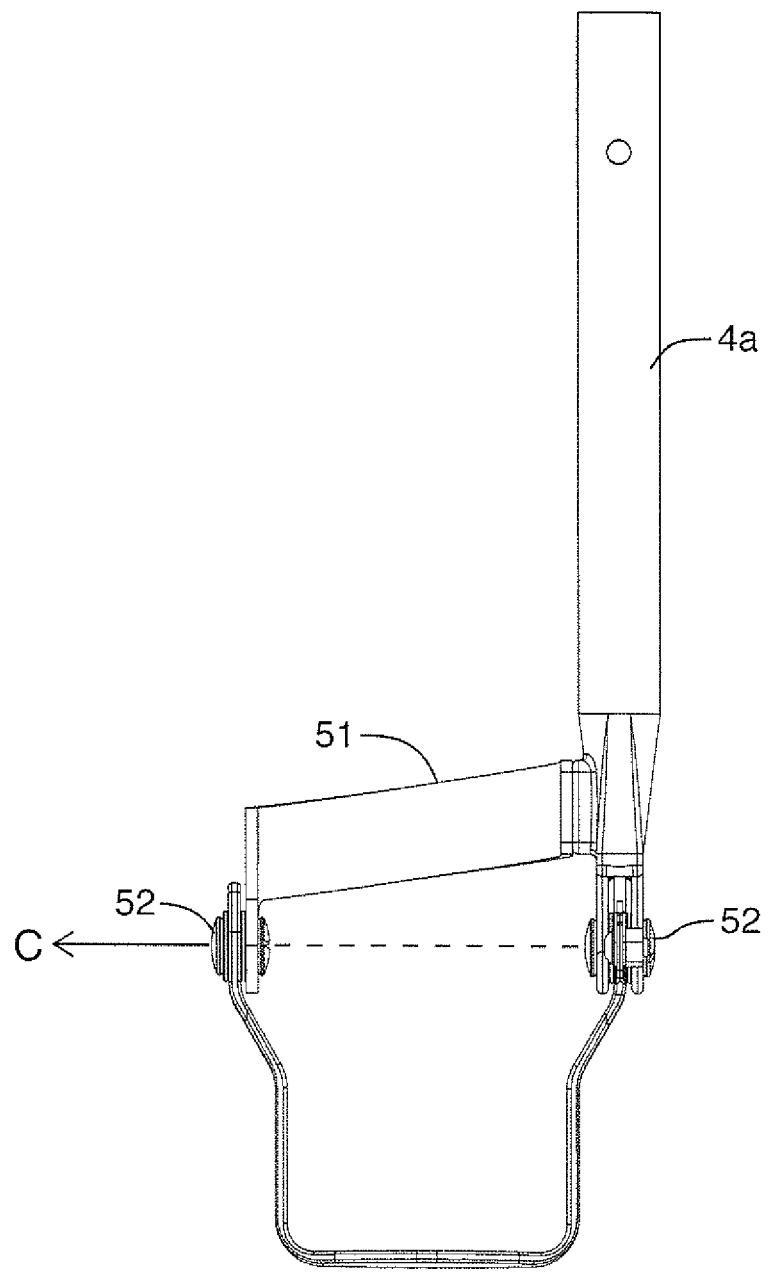
FIG. 20 is a front view of the foot portion of FIG. 18.

As exemplified in FIGS. 8 and 12, limb portion pivot axis A is positioned proximate to and generally above the transfer axis B of the transfer member or transfer shaft 26. Transfer axis B may extend generally parallel to limb portion pivot axis A. However, limb portion pivot axis A is spaced apart from the transfer member or transfer shaft 26, such that limb portion pivot axis A is vertically offset from transfer axis B. Accordingly, in the illustrated example, the lower limb portion 4 is pivotally mounted to the upper limb portion 3 about a limb portion pivot axis A, and the exoskeleton 1 is configured such that the limb portion pivot axis A is positioned proximate to, and generally above, the transfer axis B of the transfer member or transfer shaft 26.

In use, limb portion pivot axis A may be aligned with a natural pivot axis of the user's own knee and secured in this position through the use of straps or the like. Alignment of pivot axis A with the knee's natural pivot axis reduces stress on the knee joint. In contrast, current exoskeleton joints may not offer a rotational axis that is fully aligned with the user's own natural pivot axis, or may have a different rotational arc than the knee joint, such that the knee joint may be stressed at different points in the rotation.

Similarly, in other configurations such as those of drive force transmission mechanism 20', body portion 9 may be pivotally mounted to the upper limb portion 3 about a body portion pivot axis A'. The body portion pivot axis A' may be positioned proximate to, and generally below the axis of the transfer member B'. The transfer member axis may extend generally parallel to the body portion axis A'. However, the body portion axis A' is spaced apart from the transfer member or transfer shaft, such that the transfer member axis B' and body portion axis A' are vertically offset and the body portion axis A' may be positioned below the transfer member axis B' (see for example FIG. 2). As with limb portion pivot axis A, the body portion axis A' may also be aligned with a natural pivot axis of the user's hip joint.

Also in similar fashion to mechanism 20, a first driven gear may be an internal gear, surrounded by a perimeter, and the body portion pivot axis A' may be located at a lower portion of the perimeter and may be provided in gear housing 33'.

The upper limb portion 3 is thus rotatable relative to the body about an upper limb axis, with the upper limb portion pivotally mounted to the body portion about a body portion pivot axis. The exoskeleton may be configured such that the body portion pivot axis A' is positioned proximate the axis of rotation of the upper limb and the body of a user (e.g., the pivot of the hip joint) and generally below the transfer member axis B'.

It will be appreciated that if a different gear construction is utilized in combination with this aspect, then the relative positioning of the body pivot axis and the joint pivot axis of the exoskeleton may be reversed. For example, the exoskeleton may be configured such that the body portion pivot axis A' of the hip is positioned above the transfer member axis B' Similarly, the exoskeleton may be configured such that the body portion pivot axis A of the knee is positioned below the transfer member axis B.

Foot Plate Assembly

In accordance with another aspect of the teachings described herein, the following is a description of foot plate assembly, which may be used by itself in any exoskeleton or in any combination or sub-combination with any one or more other aspects disclosed herein, including the transmission construction, the offset pivot axis construction and the air bladder strap construction.

According to this aspect, an exoskeleton for the legs of a user is provided with a foot plate that is configured for receiving a foot of the user wherein the foot plate is moveable about the ankle joint of the user so as to facilitate walking. The forward portion of the foot plate may be biased so as to be raised upwardly when the leg of the user is raised off the floor and moved forward. An advantage of this design is that raising of the forward portion of the foot helps to navigate uneven terrain. For example, the foot of a user may not be moved into an object causing the user to fall over. Therefore, this aspect may help to avoid small tripping obstacles that may be found throughout the walking terrain.

Figure 25:
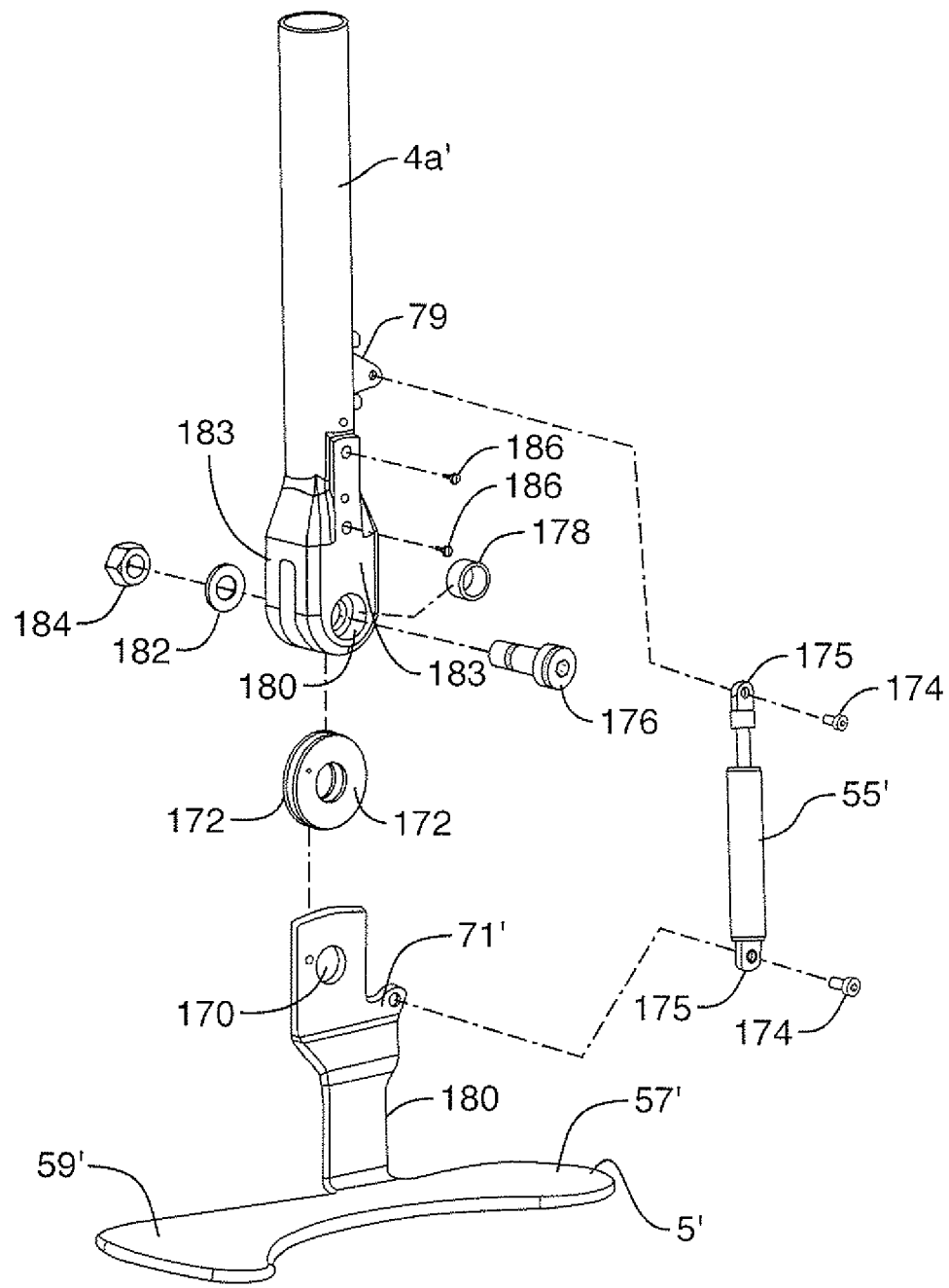
FIG. 25 is an exploded perspective view of the foot portion of FIG. 22.

The foot plate may be biased upwardly by a mechanical biasing member such as a mechanical spring 55 (see FIG. 21) or a pneumatic spring 55" (see FIG. 25). An advantage of the use of a mechanical biasing member is that the biasing member is simpler and less prone to breakdown. Further, it is lighter thereby reducing the weight of the foot plate assembly and reducing the force that is transmitted through the knee joint.

The foot plate may be biased to a raised position by a biasing member that is connected to the leg structure (e.g., lower limb portion 4) and preferably a lower end of lower limb portion 4. It will be appreciated that the biasing member may be biasingly connected to a forward portion of the foot plate assembly 75 and accordingly the biasing member may be biased to a contracted position thereby providing an upwardly directed force to a forward portion of the foot plate assembly 75. Alternately, the biasing member may be biasingly connected to a rearward portion of the foot plate assembly 75 and accordingly the biasing member may be biased to an extended or expanded position thereby providing a downwardly directed force to a rearward portion of the foot plate assembly 75.

The footplate is sized to receive a foot of the user. The foot plate may be sized so as to enable all or most of the foot of the user to be received thereon. Alternately, the foot plate may be sized to underlie only a central portion of the foot of the user. The foot plate may be sized so as to be received in a shoe.

Described herein are embodiments that provide a foot plate biased to an upward position, where the biasing can be achieved without the use of a motor or a geared transmission.

Referring to FIGS. 18-21, a first example of a foot plate assembly 75 is shown wherein an upwardly directed force is provided to a forward portion of the foot plate assembly 75.

Foot plate assembly 75 generally includes a lower leg portion end 4a, which may be a segment or portion of a lower limb portion 4 (more particularly, a lower leg portion), or which may be adapted to be coupled to lower limb portion 4.

In the illustrated example, lower leg portion end 4a is a hollow tube, which is adapted to receive a biasing assembly 54 within the tube. An advantage of this design is that the biasing member is provided as an internal member of the leg structure and therefore a separate protective housing is not required for the biasing member, thereby reducing the weight of the leg structure. In other embodiments, the biasing assembly 54 may be provided external to or adjacent to lower leg portion end 4a (see for example the embodiment of FIG. 22). In some embodiments, a lower leg portion end 4a may not be provided and lower portion 4 may be directly connected to foot plate assembly 75.

Lower leg portion end 4a is moveably coupled to a foot plate 5 at a connection point 52 and is preferably pivotally mounted thereto.

Foot plate 5 may be formed of a single generally U-shaped or stirrup-shaped element, or may be formed from multiple elements coupled together to form the foot plate. Foot plate 5 generally has an underfoot support portion and two flanges 70, with holes 100 therethrough at their upper ends. One of the flanges 70, preferably the outwardly positioned one, is used to connect foot plate 5 to lower leg portion end 4a at connection point 52, which defines an ankle pivot axis C. Pivot axis C is generally transverse to the longitudinal axis of lower leg portion end 4a.

Figure 22:
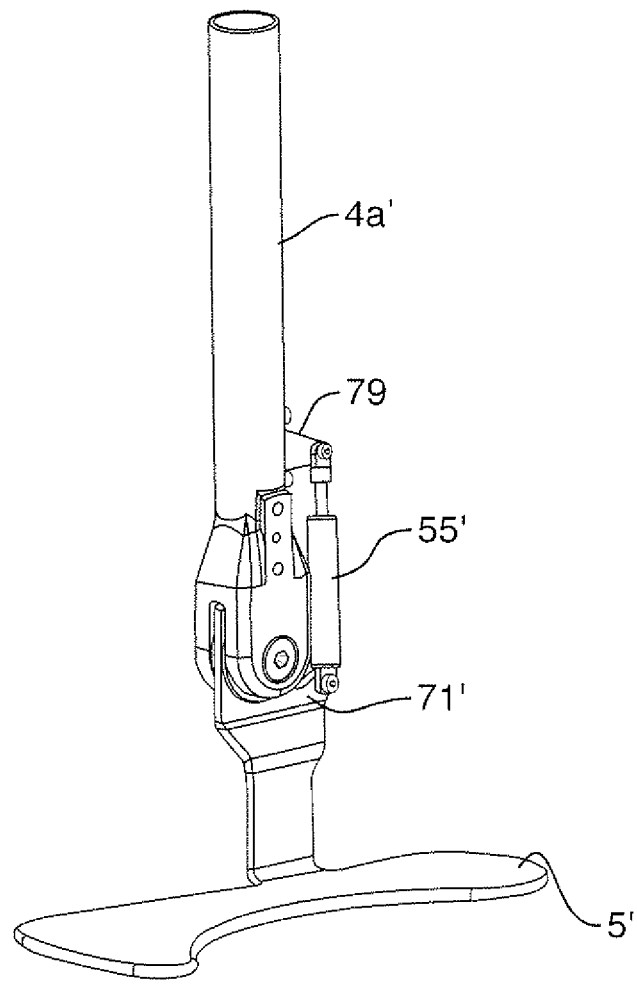
FIG. 22 is a perspective view of a foot portion for the leg of an exoskeleton in accordance with an alternative embodiment.
Figure 23:
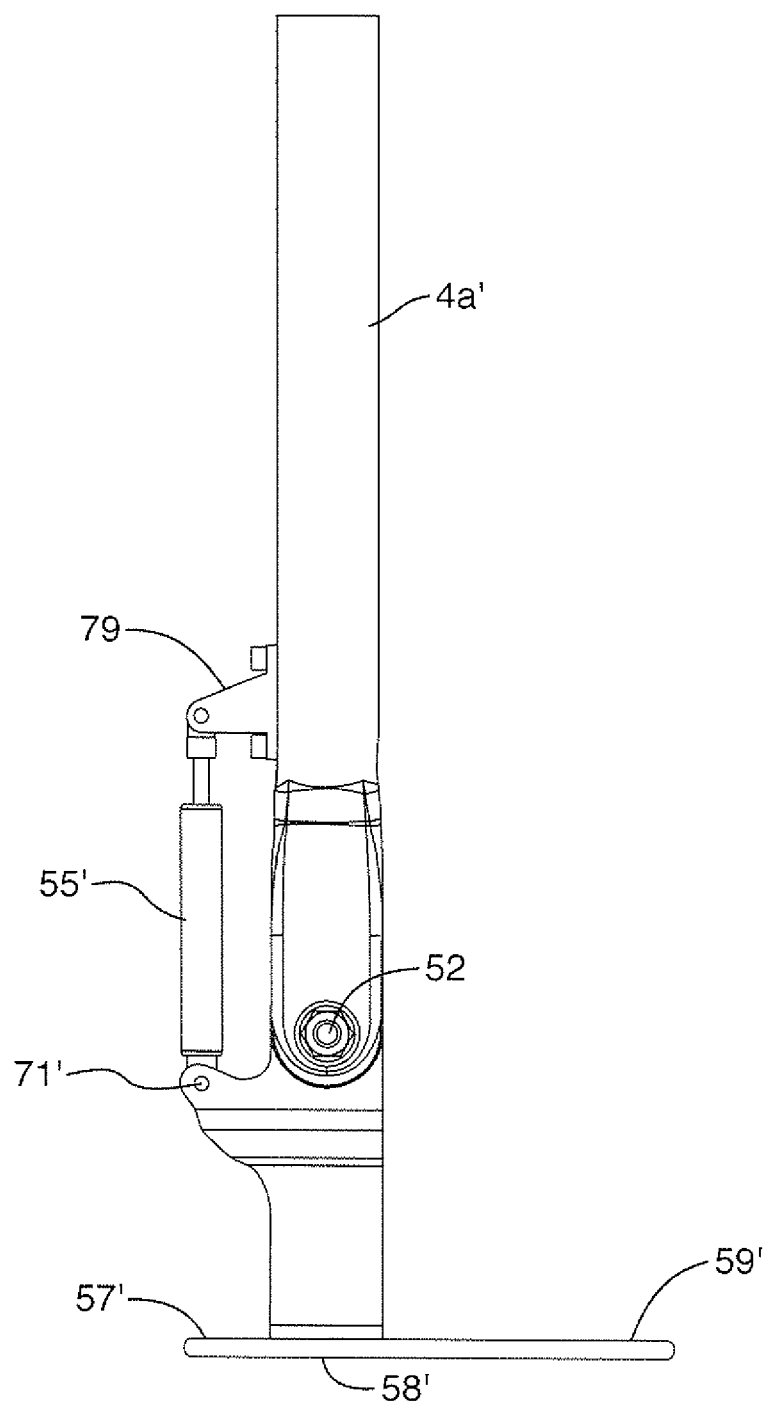
FIG. 23 is an outside side view of the foot portion of FIG. 22.
Figure 24:
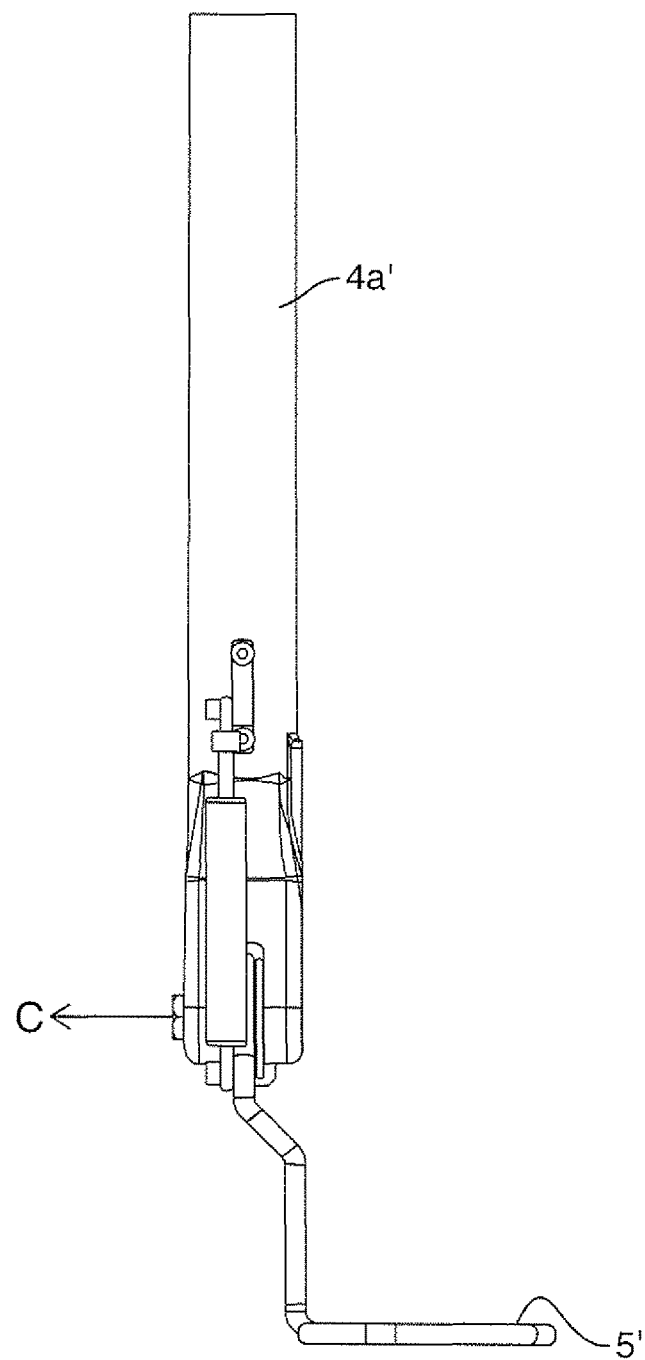
FIG. 24 is a front view of the foot portion of FIG. 22.

Accordingly, it will be appreciated that only one flange 70 may be provided (see for example the embodiment of FIG. 22). Therefore, in some embodiments, only one flange 70 is provided, and may be configured to be positioned to an outer side of a user of the exoskeleton.

Flanges 70 may extend laterally and upwardly from the foot plate underfoot support portion. Flanges 70 are preferably shaped such that opening 100 is positioned adjacent the ankle joint of a user and laterally, and preferably outwardly, spaced therefrom so as to not engage the ankle of a user during walking.

Figure 21:
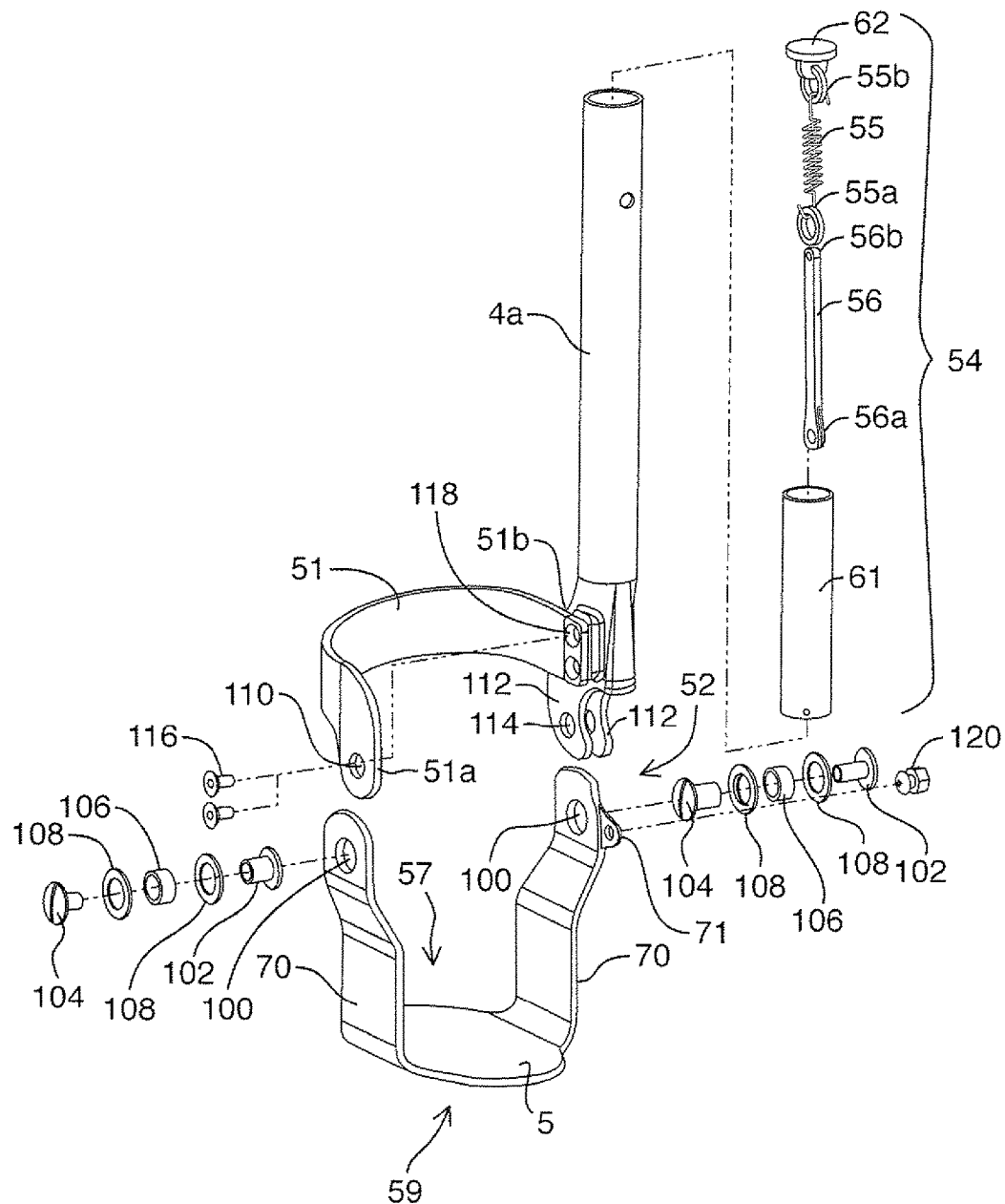
FIG. 21 is an exploded perspective view of the foot portion of FIG. 18.

As exemplified in FIG. 21, lower leg portion end 4a is rotatably moveably coupled to foot plate 5 at the connection point 52 using a suitable bearing, washer assembly or other rotatable coupling. For example, the lower end of lower leg end portion 4a may be provided with a pair of spaced apart flanges 112 and outer flange 70 may be pivotally mounted thereto. As exemplified, flanges 112 have openings 114 therein. Inner flange 70 is received between flanges 112 and openings 114 and 100 aligned. An inner screw member with an internal threaded bore may be provided on an inner side of outer flange 70 and extend outwardly through openings 114 and 100. A washer 108 may be provided between inner screw member 102 and the inner surface of inner flange 70. A bearing 106 may be provided on the shaft of inner screw member 102 and positioned in opening 100. A washer may then be positioned on the shaft of inner screw member 102 and outer screw member 104, which has an outer threaded shaft, may then be screwed into the threaded bore of inner screw member 102. It will be appreciated that other pivot mounts may be used.

The underfoot support portion of foot plate 5 has a rearward portion 57 provided rearwardly of connection point 52 for supporting the user's heel and a forward portion 59 provided forward of connection point 52 for supporting at least a portion of the user's forefoot. Flange 70 is accordingly provided at middle section 58, between rearward portion 57 and forward portion 59.

Foot plate 5 and the underfoot support portion in particular may be generally sized to fit within a user's shoe, such that in use the user's foot is placed within the flanges 70 and above, e.g., on the top surface of, the underfoot support portion, whereupon the foot plate 5 may be placed within the user's shoe. Accordingly, the user's shoe provides traction for walking.

An ankle support 51 may be provided. In such a case, ankle support 51 may be coupled to lower leg portion end 4a at one end and to foot plate 5 at an opposite end, in which case two flanges 70 may be provided. Alternatively, ankle support 51 may be coupled to foot plate 5 at both ends, for example at connection point 52. Ankle support 51 is generally formed of a stiff material, such as metal or plastic, although flexible materials may also be used in some embodiments and padding may be provided.

As exemplified in FIG. 21, ankle support 51 is provided with an opening 110 at its distal end 51a and may be co-mounted on inner screw member 102 with inner flange 70. It will be appreciated that if an ankle support 51 is not provided, then inner flange 70 may not be provided. The proximal end 51b of ankle support 51 may be secured to lower leg end portion 4a such as by screws 116 that extend through openings 118 in proximal end 51b of ankle support 51 and into lower leg end portion 4a. As such, ankle member 51 is fixed in position. In an alternate embodiment, ankle support 51 may be pivotally or otherwise moveably mounted.

Ankle support 51 may be generally positioned as to be above the heel of the user's shoe, so as not to interfere with the shoe when a walking motion is carried out.

In accordance with the embodiment of FIGS. 18-21, the forward portion 59 of foot plate 5 is biased upwardly. Accordingly, outer flange 70 may include a biasing flange 71, which is provided forward of opening 100 and preferably is provided generally slightly forward of connection point 52 and proximate the ankle of a user of the exoskeleton. Biasing member 55 is biasingly connected between lower limb portion 4 and foot plate assembly 75 and may be directly connected to each or may be connected to a first extension member that extends from biasing member 55 to connect to foot plate assembly 75 and/or a second extension member that extends from biasing member 55 to connect to lower limb portion 4.

As exemplified, first end 55a of biasing member 55 is connected to second end 56b of rod 56 and second end 56a of rod 56 is connected to flange 71 (e.g., via screw 120). Second opposed end 55b of biasing member 55 may be coupled to a cap 62, which can be anchored to a portion of lower leg portion end 4a (e.g., it may seat on the upper opening of lower leg portion end 4a). In some embodiments, cap 62 may be a screw cap coupled to threads provided within lower leg portion end 4a. Adjustment of the screw cap thereby provides tension adjustment of biasing member 55. Optionally, sheath 61 is provided inside lower leg portion end 4a and receives biasing member 55 therein. An advantage of this design is the biasing member, or an extension member, is moveably mounted to the lower leg portion end 4a and the foot plate assembly so that it may pivot or move as a user walks. In view of this construction, the orientation of the biasing member or an extension thereof is moveable with respect to each of the lower limb portion 4 and the foot plate assembly 75. This construction is preferred is the biasing member is a rigid member such as a pneumatic spring as exemplified in FIG. 25. In other embodiments, the orientation may be fixed. Such as embodiment may be used if the biasing member is flexible, such as a coil spring.

It will be appreciated that the biasing member 55 may be secured directly to flange 71 and/or biasing member may be secured to another portion of foot plate assembly 75. Similarly, biasing member 55 may be secured to another portion of the lower leg portion end 4a or lower limb 4.

In the illustrated embodiment, biasing member 55 is a coil spring. However, in other embodiments, biasing member 55 may be an elastic element, a pneumatic spring biased to a compressed position, or other suitable biasing member.

The foot plate is moveably mounted at connection points 52, such that it is articulable between a first position in which the rearward portion 57 extends downwardly and the forward portion 59 extends upwardly, and a second position in which the rearward portion 57 extends upwardly and the forward portion 59 extends downwardly.

Biasing member 55 is generally biased to a compressed configuration, in which foot plate 5 is raised to the first position. By biasing foot plate 5 to the first position, the weight of the user and the exoskeleton causes the foot plate 5 to flatten against a surface when a user places weight on the foot plate 5, such as when in a standing position or when the user is walking and places their foot on the floor. However, when the leg is raised, biasing member 55 causes the foot plate 5 to return to the first raised position, with the forward portion 59 is raised upwardly.

In some embodiments, the biasing member may be pivotally connected to the foot plate at a position other than connection point 52. For example, in some alternative embodiments, the biasing member may be drivingly connected to foot plate 5 at a position rearward of the connection point 52. More particularly, the biasing member may be connected to a flange provided at the middle section that extends laterally and upwardly from the underfoot portion of foot plate 5, or a biasing flange positioned rearwardly of connection point 52. FIGS. 22-25 exemplify such an alternate embodiment.

Referring now to FIGS. 22-25, there is shown another example of a foot plate assembly wherein a downwardly directed force is provided to a rearward portion of the foot plate assembly.

In this alternative configuration, the biasing member 55 is moveable between an extended configuration in which the rearward portion 57 extends downwardly and the forward portion 59 extends upwardly and a contracted configuration in which the rearward portion 57 extends upwardly and the forward portion 59 extends downwardly. In this configuration, the biasing member is biased to the extended configuration. Such a biasing member 55' may be a telescoping pneumatic spring, for example.

The telescoping spring may be moveably, and preferably, pivotally mounted to the lower leg portion end 4a, such as by a flange 79. In this embodiment, flange 71' is provided rearward of the connection point 52 and telescoping spring may be moveably, and preferably, pivotally mounted to flange 71'. In some embodiments, biasing member 55' may be a pneumatic cylinder.

Biasing member 55' has support mounts 175 at opposite ends. Screw members 174 may be used to secure support mounts 175 to flange 79 and flange 71', respectively.

Foot plate 5' may be formed of a single generally U-shaped or stirrup-shaped element, or may be formed from multiple elements coupled together to form the foot plate. Foot plate 5' generally has an underfoot support portion and one outboard flange 180, with a hole 170 therethrough at its upper end for connection point 52. Flange 180 extends laterally and upwardly from the foot plate underfoot support portion. Flange 180 is preferably shaped such that opening 170 is positioned adjacent the ankle joint of a user and laterally and, preferably outwardly, spaced therefrom so as to not engage the ankle of a user during walking.

As exemplified in FIG. 25, lower leg portion end 4a' is rotatably moveably coupled to foot plate 5' at the connection point 52 using a suitable bearing, washer assembly or other rotatable coupling. For example, a lower end of lower leg 4a' may be provided with forks 183, which have an opening 180 therethrough. Forks 183 may be secured to the lower leg 4a' by means of fasteners 186, although in other embodiments, forks 183 may be integral to lower leg 4a'.

Opening 180 is aligned with opening 170 and forks 183 are spaced apart from flange 180 by a pair of washers 172. An inner screw member 176 with an outer threaded shaft may be provided on an inner side of inner flange 70 and extend outwardly through opening 180. A bearing 178 may be provided on the shaft of inner screw member 176 and positioned in opening 180. A washer 182 may then be positioned on the shaft of inner screw member 176 and an outer screw member 184, which has an inner threaded shaft, may then be screwed into the threaded bore of inner screw member 176. It will be appreciated that other pivot mounts may be used.

In some embodiments, the biasing member may be moveably mounted to the foot plate 5 at a position proximate the ankle of the user and may be positioned offset from the ankle above or below the ankle, and forward or rearward of the ankle.

Air Bladder Straps

In accordance with another aspect of the teachings described herein, the following is a description of a strap which may be used by itself in an exoskeleton or in any combination or sub-combination with any one or more other aspects, including the transmission construction, the offset pivot axis construction and the foot plate assembly construction.

In order to support the weight of a user while in use, the exoskeleton should be secured to the user at various points. For example, the exoskeleton may be secured to the user at the waist, mid-thigh level, and mid-calf level. In another example, the exoskeleton can be secured at the waist, at an upper thigh level proximate to the hip, at a lower thigh level proximate to the knee, at a sub-patellar level proximate to and below the knee, and at an ankle level.

In some embodiments, plastic or fabric straps may be used to secure the exoskeleton to the user. However, such straps may apply pressure to the user's limbs and torso at certain points, causing pain or discomfort, or even bruising and abrasion injuries if the user has impaired feeling in the limb. Moreover, straps that are poorly fitted may have a tendency to "ride" up or down a limb which may impact performance of the exoskeleton and even pose a risk to the user. Further, the movement of the strap relative to the user may cause damage to the skin of the user.

In accordance with this aspect, a strap is provided which has an air bladder or pocket therein. The air bladder is inflated to a pressure within a desired range. The pressure is set so as to be sufficient to secure a user in position. The upper level of the preferred pressure range may be set so as to be below a level at which the circulation of the user is restricted. The lower level of the preferred pressure range may be set so as to be above a level at which the strap is too lose and will move while in use.

An advantage of the use of straps that include one or more air bladders is that the tendency for pressure sores to occur may be reduced. Pressure sores occur from over compression of the skin. A user may not have any sensation at the location at which a strap is used to secure them to an exoskeleton. Therefore, when a strap is applied, it may be applied at a compression that is acceptable while at rest but which produces over compression during walking. For example, a paraplegic does not have any sensation below the point of injury and will not feel when a strap is too tight and is over compressing the skin. Pressure sores are a significant reason for the re-hospitalization of paraplegics.

Referring to FIGS. 26-29, examples of straps are shown for use with an exoskeleton, such as exoskeleton 1. As described herein, exoskeleton 1 may have at least one leg structure, and a drive member such as a drive motor 21, operatively connected to the at least one leg structure.

One or more air bladder straps 81 may be attached or coupled to the exoskeleton and configured to secure a user to a portion of the exoskeleton.

Figure 26:
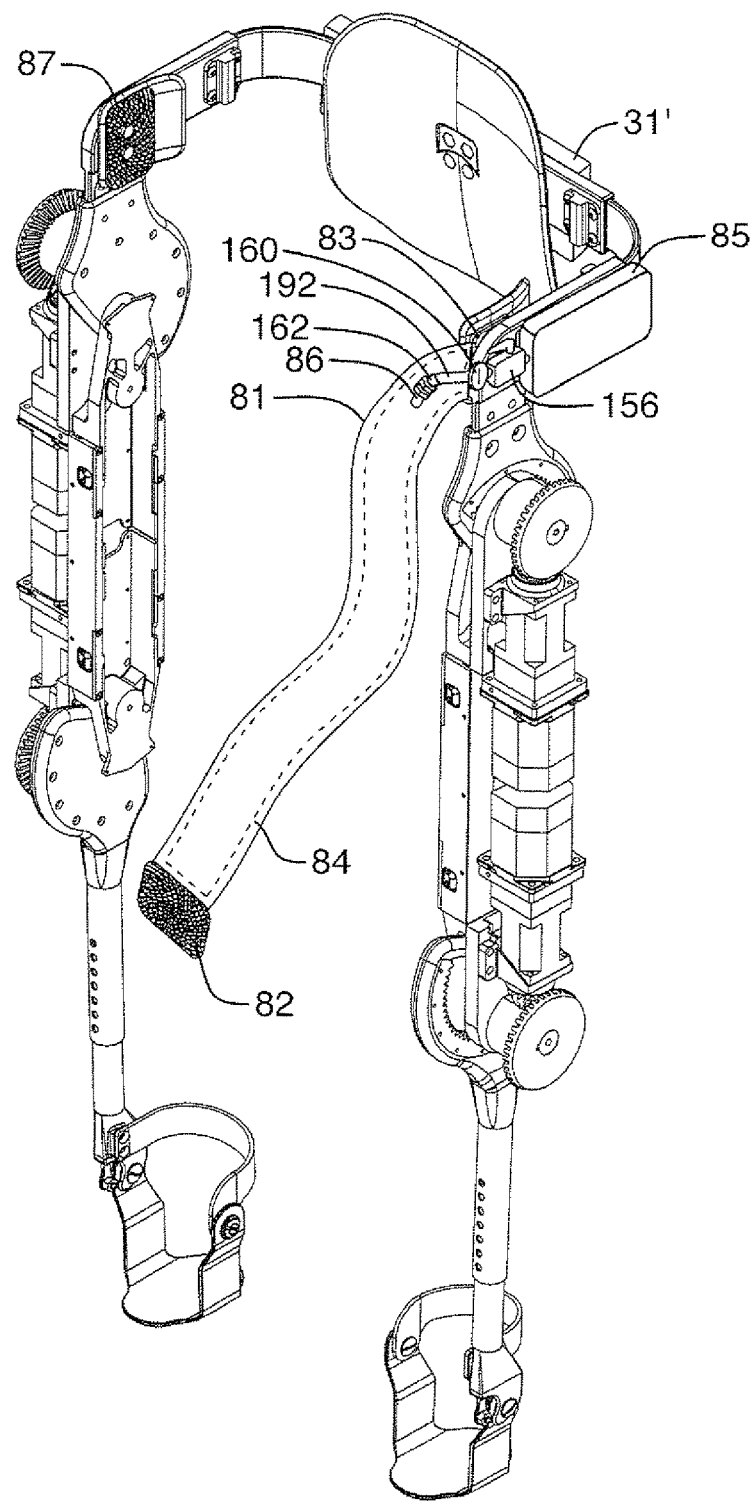
FIG. 26 is a perspective view of an exoskeleton with an example air bladder strap.

In the example of FIG. 26, air bladder strap 81 has a section that extends from an openable portion 82 to an attachment portion 83 provided on the exoskeleton, the section having an inflatable pocket 84 having a first end proximate the openable portion and a second end proximate the attachment portion. The first and second ends are in air flow communication. An advantage of this design is that essentially the entire length of the strap that surrounds a portion of the user may have an air bladder that permits air to flow from one end to the other. Therefore, the pressure in the entire air bladder will remain uniform. Accordingly, if the strap is compressed at one location during use of the exoskeleton, the local pressure in the air bladder at that location will increase but be dissipated throughout the air bladder, thereby reducing the compression applied to the body of the user.

A power pack or battery 31' is also shown in FIG. 26, mounted on a waist member or body portion of the exoskeleton. It will be appreciated that battery 31' can be provided instead of batteries 31 mounted on the upper leg portions, or may be provided in addition to such batteries. It will be further appreciated that battery 31' may be mounted in a variety of positions, for example on a back portion of the waist member, along the sides, or combinations thereof.

Figure 27:
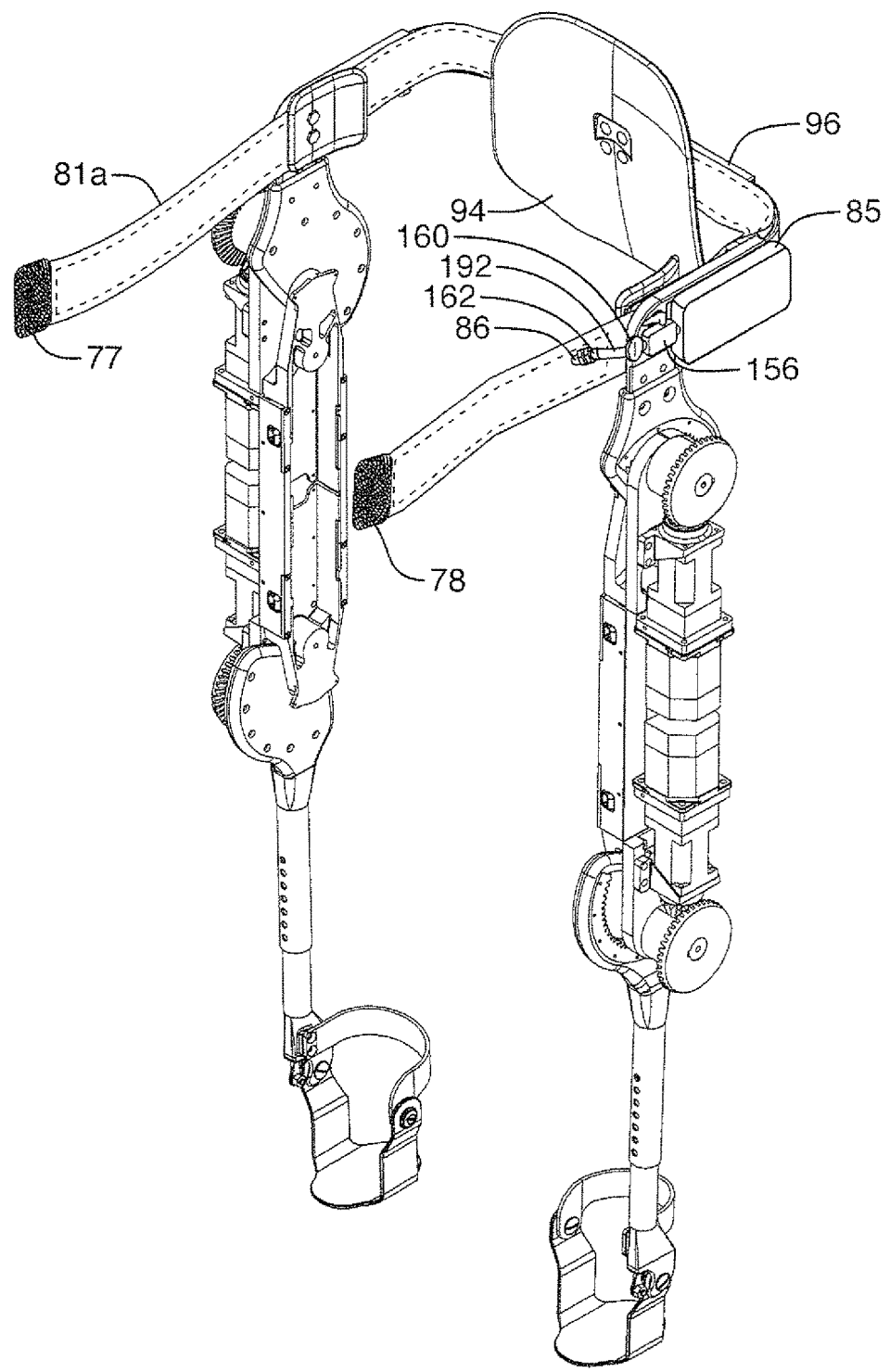
FIG. 27 is a perspective view of an exoskeleton with another example air bladder strap.

In another example shown in FIG. 27, air bladder strap 81a extends continuously around the user's body, passing behind back support 94 but between back support 94 and back adjustment 96. An openable portion 77 of air bladder strap is releasably attachable to an attachment portion 78.

It will be appreciated that, in some embodiment, a single continuous air bladder or inflatable pocket 84 may not extend from a position proximate openable portion 82 to a position proximate attachment portion 83. Further, in other cases, an air bladder may extend only along a portion of a strap. In such an embodiment, the strap may include 2 or more air bladders that are positioned end to end so as to extends part or all of the way from a position proximate openable portion 82 to a position proximate attachment portion 83.

In some embodiments, the inflatable pocket 84 is integral to the air bladder strap, for example where the air bladder strap is formed of plastic elements heat sealed to form the inflatable pocket. Accordingly, an outer cover member that is secured to the exoskeleton may not be used.

In other embodiments, the inflatable pocket 84 may be a bladder inserted in a strap, wherein the strap is formed from two or more sections. For example, the strap may be formed from two or more lengths of fabric sewn together, and a bladder inserted between the fabric pieces.

A source of pressurized fluid, such as an air compressor 85 or compressed air cylinder is connectable in flow communication with the inflatable pocket via an inlet 86. The source of pressurized fluid may be on board the exoskeleton or external, and preferably on body portion 9.

Referring again to FIG. 26, openable portion 82 of the air bladder strap may be releasably attachable to the exoskeleton at a first location on the exoskeleton, such as attachment point 87. Any attachment suitable for securing the exoskeleton to the user may be used, including for example a buckle, a snap connector, or hook-and-loop fastener or the like.

In some embodiments, the air bladder strap is non-releasably attached to the attachment portion 83 provided on the exoskeleton. For example, the air bladder strap may be fastened to the attachment portion 83 using screws, adhesives or the like.

Figure 28:
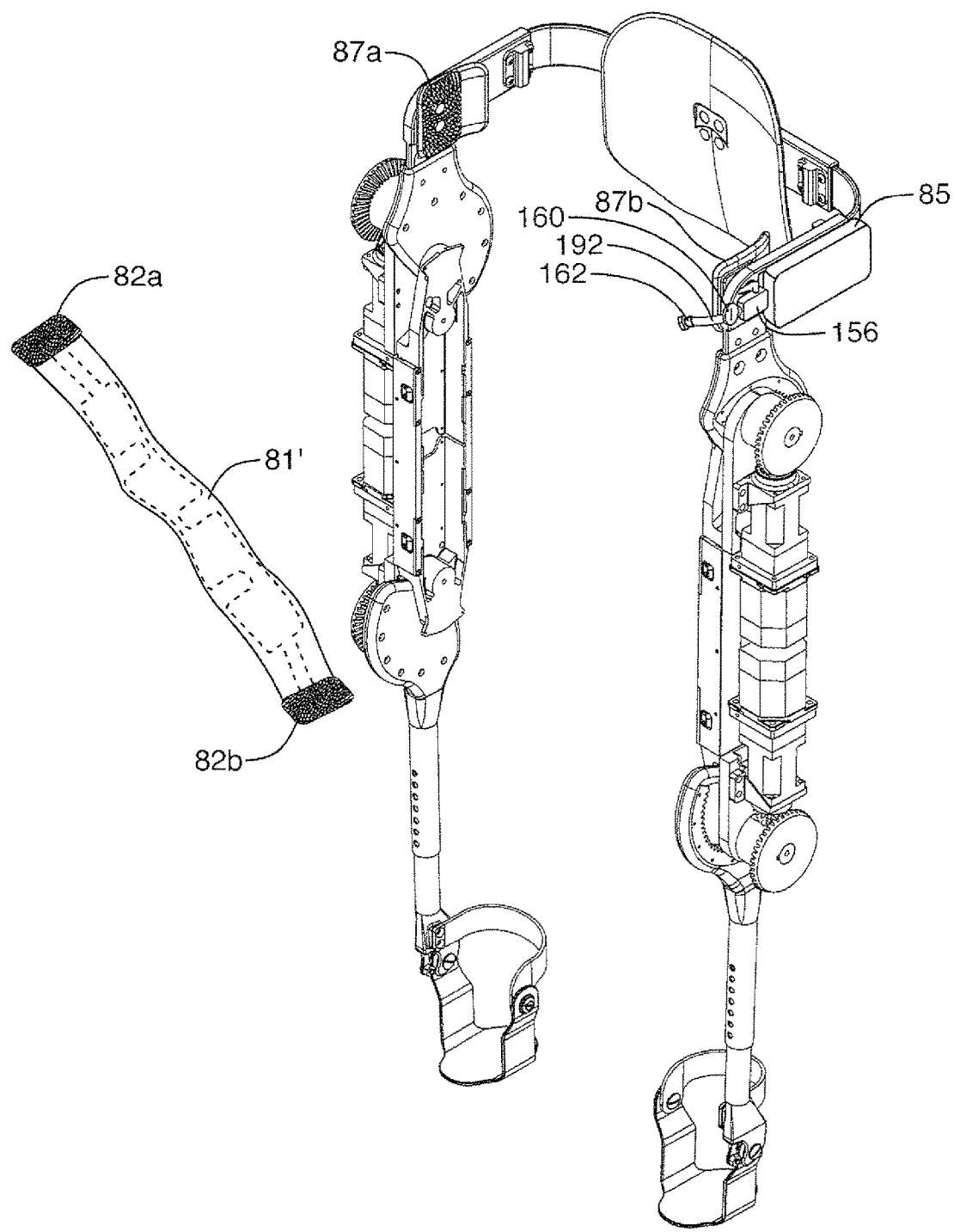
FIG. 28 is a perspective view of an exoskeleton with yet another example air bladder strap.

In other embodiments, such as that shown in FIG. 28, the air bladder strap 81' is releasably attached to a first location 82a and a second location 82b. In such embodiments, a fluid flow coupling may be provided at the first or second location, or both, to provide fluid communication between the source of pressurized fluid and the inflatable pocket.

Figure 29:
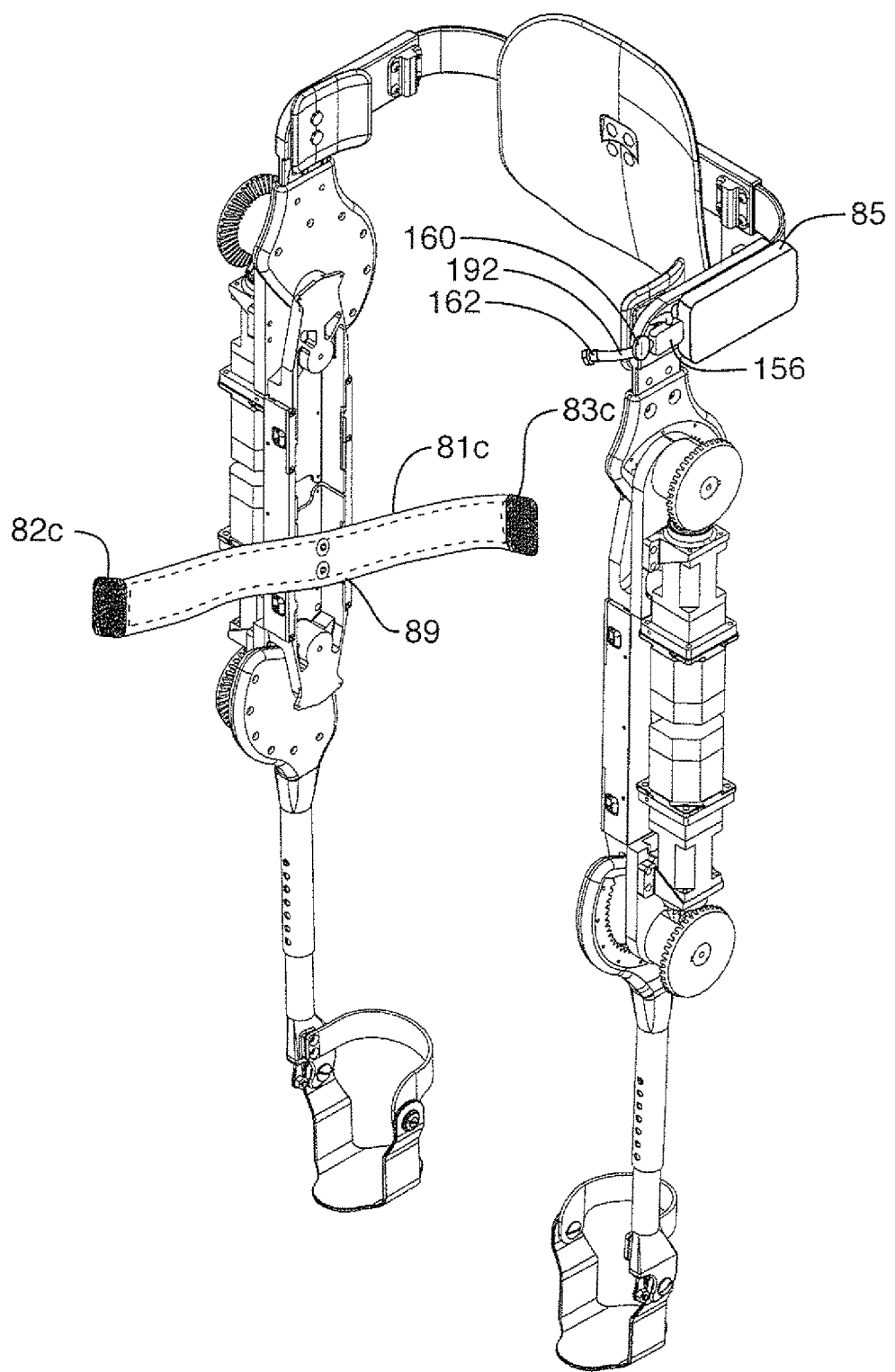
FIG. 29 is a perspective view of an exoskeleton with yet another example air bladder strap; and, FIG. 30 is a schematic drawing of a control system for an exoskeleton with an air bladder strap.

In still other embodiments, such as that shown in FIG. 29, the air bladder strap 81c may be connected to the exoskeleton at a mid-portion 89 of the strap, and an openable portion 82c may be releasably attachable to an attachment portion 83c provided on an opposing end of the strap, such as by a snap connector, or hook-and-loop fastener or the like.

In some embodiments, the inflatable pocket may be baffled, as shown in FIG. 28. In such a case, the laterally opposed ends of the strap are still in air flow communication with each other.

In some embodiments, the air bladder strap may have at least one additional inflatable pocket. For example, strap 81 may be provided with a second pocket 84 that is parallel to and may be coextensive with (e.g., above or below) pocket 84. The source of pressurized fluid may be in flow communication with all of the inflatable pockets or different sources of pressurized fluid may be provided and one source of pressurized fluid may be in flow communication with only one or more of the inflatable pockets.

It will be appreciated by a skilled person in the art that various combinations and configurations of the air bladder strap are possible, and more than one configuration may be used with a single exoskeleton.

In use, the air bladder strap is generally extended around a portion of the user's body and connected to the exoskeleton. The air bladder strap is then pressurized or inflated to a predetermined pressure from a source of pressurized fluid, under the control of a controller (see FIG. 30) which may be provided on the exoskeleton, preferably on body portion 9, or which may be an external controller. The controller is generally operatively connected to the source of pressurized fluid.

The controller may be configured to maintain pressure in the air bladder strap within a predetermined range. Alternately, the controller may be configured to maintain pressure in the air bladder strap above a predetermined level. The source of pressurized fluid may be in air flow communication with each strap 81. Alternately, a separate source of pressurized fluid may be in air flow communication with each strap 81.

Figure 30:
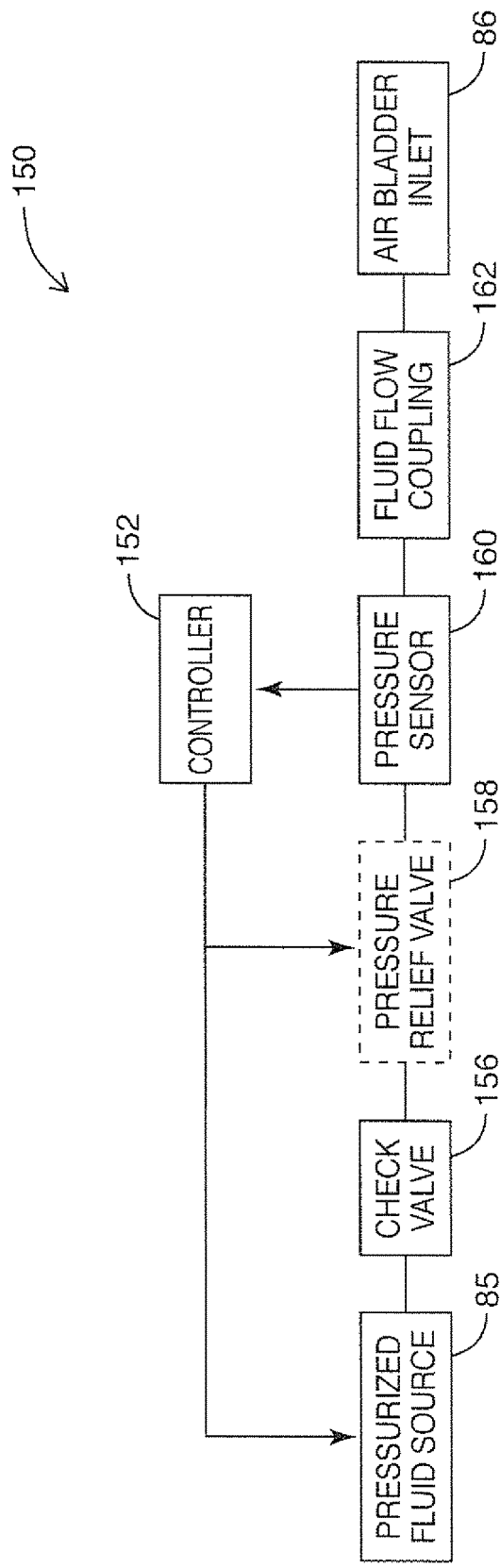

Referring to FIG. 30, there is shown an example control system 150 for monitoring pressure in the air bladder strap using a pressure sensor 160 in flow communication with the inflatable pocket 84. A controller 152 monitors pressure in pocket 84 using pressure sensor 160. Pressure sensor may be provided between a source of pressurized fluid 85 and the pocket 84, and preferably between the source of pressurized fluid 85 and a fluid flow coupling 162 (e.g., the inlet to pocket 84). For example, it may be in the flow conduit 192 between the source of pressurized fluid 85 and the pocket 84. Controller 152 may be configured to actuate the source of pressurized fluid 85 in response to a low pressure signal from the pressure sensor 160.

The fluid flow coupling 162 is generally provided at an air bladder inlet 86. A check valve 156 may also be positioned between the pressure sensor 160 and the source of pressurized fluid 85 to isolate the source of pressurized fluid 85 when it is not in use.

In some embodiments, a pressure relief valve 158 may be provided in flow communication with the inflatable pocket. Pressure relief valve is configured to release pressure from the air bladder strap when an overpressure condition occurs. Pressure relief valve 158 may be a mechanical valve (e.g., spring actuated) in which case the controller may be configured to maintain pressure in the air bladder strap above a predetermined level. Alternately pressure relief valve 158 may be electronic (e.g., it may be actuatable by the controller 152 to automatically release pressure from the air bladder strap when the pressure in the inflatable pocket exceeds a predetermined pressure, such as determined by pressure sensor 1600), in which case the controller may be configured to maintain pressure in the air bladder strap within a predetermined range.

In some embodiments, the pressure relief valve 158 and the check valve 156 may be a single three way valve.

Accordingly, the controller 152 may be configured to maintain the fluid pressure within inflatable pocket 84 at a predetermined pressure, or within a predetermined range. The predetermined pressure can be selected to provide a secure fit of the exoskeleton to the user while preventing injury or discomfort to the user.

In some embodiments, as exemplified in FIG. 26, body portion 9 has the power supply, the source of compressed air 85 and controller mounted thereon. An advantage of this design is that the weight of these components is provided on the part of the exoskeleton that is secured to a user's waist. Therefore, this portion of the weight is transmitted to the user's lower torso. This reduces the weight that would otherwise be placed on the limbs of the exoskeleton, which would increase the force transmitted through the joints of the exoskeleton.

What has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

What is claimed is:

1. An exoskeleton for a limb of a user wherein the limb has an upper limb connected to the body of the user and a lower limb, the upper limb is rotatable to the body about a first axis and the upper limb and the lower limb are rotatable to each other about a second axis, the exoskeleton comprising:
   a) a body portion;
   b) at least one limb structure comprising a longitudinally extending upper limb portion and a lower limb portion, wherein the upper limb portion is pivotally mounted to the body portion about a first limb portion pivot axis or the upper limb portion is pivotally mounted to the lower limb portion about a second limb portion pivot axis;
   c) a first drive motor mounted on the upper limb portion and having a longitudinally extending motor axis that extends parallel with the longitudinally extending upper limb portion; and,
   d) a first drive force transmission mechanism wherein
      i) the first drive force transmission mechanism drivingly connects the first drive motor to the body portion and the first drive force transmission mechanism comprises a first transfer member extending parallel to the first limb portion pivot axis and offset from the first axis, or
      ii) the first drive force transmission mechanism drivingly connects the first drive motor to the lower limb portion and the first drive force transmission mechanism comprises a first transfer member extending parallel to the second limb portion pivot axis and offset from the second axis; and
   wherein the first drive force transmission mechanism comprises a first drive gear on a motor output axle, a first driven gear provided on the first transfer member, the first driven gear driven by the first drive gear, a second drive gear provided on the first transfer member and spaced apart from the first driven gear, and a second driven gear provided on the body portion or the lower limb portion, wherein the second driven gear is an internal gear that has an inner surface that is generally concave, wherein a plurality of gear teeth are provided on the inner surface, and wherein the second drive gear engages with the plurality of gear teeth on the inner surface to drive the second driven gear.

2. The exoskeleton of claim 1 wherein a second drive force transmission mechanism drivingly connects a second drive motor to the lower limb portion and the second drive force transmission mechanism comprises a second transfer member extending parallel to the second limb portion pivot axis and offset from the second axis.

3. The exoskeleton of claim 1 wherein the exoskeleton is configured such that the first limb portion pivot axis is positioned proximate the first axis or the second limb portion pivot axis is positioned proximate the second axis.

4. The exoskeleton of claim 1 wherein the first limb portion pivot axis is spaced from the first transfer member or the second limb portion pivot axis is spaced from the first transfer member.

5. The exoskeleton of claim 4 wherein the second driven gear is provided on a lower end of the body portion, the second driven gear is surrounded by a perimeter and the first limb portion pivot axis is located at a lower portion of the perimeter or the second driven gear is provided on an upper end of the lower limb portion, the second driven gear is surrounded by a perimeter and the second limb portion pivot axis is located at an upper portion of the perimeter.

6. The exoskeleton of claim 1 wherein a motor axis of the first drive motor extends generally parallel to the upper limb portion and is transverse to the first transfer member.

7. The exoskeleton of claim 1 wherein the first drive force transmission mechanism is a rotary motion drive force transmission mechanism.

8. The exoskeleton of claim 1 wherein the internal gear is provided on a lower end of the body portion or an upper end of the lower limb portion and the internal gear has a constant arc.

9. The exoskeleton of claim 1 wherein the internal gear comprises a stop member associated with one end thereof.

10. The exoskeleton of claim 1 wherein the internal gear comprises a stop member associated with each end thereof.

11. The exoskeleton of claim 1 wherein the internal gear has travel portion having an arc of from 30° to 150°.

12. The exoskeleton of claim 1 wherein the internal gear has a driven side on which the first transfer member is provided and an opposed side and the opposed side is closed.

13. The exoskeleton of claim 1 wherein the internal gear is provided on an upper end of the lower limb portion or a lower end of the body portion, the internal gear has first and second spaced apart gear ends, and the exoskeleton further comprises a controller operatively connected to the drive motor to prevent rotation of the first transfer member drive gear past the first gear end.

14. The exoskeleton of claim 13 wherein the internal gear comprises a first stop associated therewith at the first gear end to stop rotation of the transfer shaft drive prior to or at the first stop.

15. The exoskeleton of claim 1 wherein at least one of the second driven gear and the second drive gear is non-rotatably mounted to the first transfer member by a shearable key.

16. The exoskeleton of claim 1 wherein the at least one limb structure comprises a left leg structure and a right leg structure and the body portion comprises a waist member and a plurality of straps securing the user to the leg structures whereby the user's weight is transmitted to the exoskeleton by the left and right leg structures.

17. The exoskeleton of claim 16 wherein at least one of the straps comprises an inflatable pocket.

18. The exoskeleton of claim 1 wherein the first driven gear is a reduction gear, and wherein the first drive force transmission mechanism provides a gear reduction.

19. The exoskeleton of claim 18 wherein the gear reduction is in the range between 1:200 to 1:600.

20. An exoskeleton for a limb of a user wherein the limb has an upper limb connected to the body of the user and a lower limb, the upper limb is rotatable to the body about a first axis and the upper limb and the lower limb are rotatable to each other about a second axis, the exoskeleton comprising:
   a) a body portion;
   b) at least one limb structure comprising a longitudinally extending upper limb portion and a lower limb portion, wherein the upper limb portion is pivotally mounted to the body portion about a first limb portion pivot axis or the upper limb portion is pivotally mounted to the lower limb portion about a second limb portion pivot axis;

c) a first drive motor mounted on the upper limb portion and having a longitudinally extending motor axis that extends parallel with the longitudinally extending upper limb portion; and,
d) a first drive force transmission mechanism, wherein
   i) the first drive force transmission mechanism drivingly connects the first drive motor to the body portion and the first drive force transmission mechanism comprises a first transfer member extending parallel to the first limb portion pivot axis and offset from the first axis, or
   ii) the first drive force transmission mechanism drivingly connects the first drive motor to the lower limb portion and the first drive force transmission mechanism comprises a first transfer member extending parallel to the second limb portion pivot axis and offset from the second axis,
wherein the first transfer member rotates about a first transfer axis, wherein the first drive force transmission mechanism comprises an internal gear provided on a lower end of the body portion or an upper end of the lower limb portion, wherein the internal gear has an inner curved surface that is generally concave and an outer curved surface that is generally convex, wherein a plurality of gear teeth are provided on the inner curved surface of the internal gear.

* * * * *